US006811992B1

(12) United States Patent
Liu

(10) Patent No.: US 6,811,992 B1
(45) Date of Patent: Nov. 2, 2004

(54) METHOD FOR IDENTIFYING MLK INHIBITORS FOR THE TREATMENT OF NEUROLOGICAL CONDITIONS

(76) Inventor: Ya Fang Liu, One Emerson Place, 5G, Boston, MA (US) 02114

( * ) Notice: Subject to any disclaimer, the term of this patent is extended or adjusted under 35 U.S.C. 154(b) by 0 days.

(21) Appl. No.: 09/156,367

(22) Filed: Sep. 17, 1998

Related U.S. Application Data
(60) Provisional application No. 60/085,439, filed on May 14, 1998.

(51) Int. Cl.[7] ............................. C12Q 1/00; C12Q 1/68; C12Q 1/48; G01N 33/53; C12P 21/06
(52) U.S. Cl. ................................ 435/15; 435/4; 435/6; 435/7.1; 435/69.1
(58) Field of Search ........................... 435/4, 15, 6, 7.1, 435/69.1

(56) References Cited

U.S. PATENT DOCUMENTS

| | | |
|---|---|---|
| 4,980,281 A | 12/1990 | Housey |
| 5,385,915 A | 1/1995 | Buxbaum et al. |
| 5,461,146 A | 10/1995 | Lewis et al. |
| 5,468,872 A | 11/1995 | Glicksman et al. |
| 5,475,110 A | 12/1995 | Hudkins et al. |
| 5,516,772 A | 5/1996 | Glicksman et al. |
| 5,534,426 A | 7/1996 | Karin et al. |
| 5,554,523 A | 9/1996 | Reddy et al. |
| 5,591,855 A | 1/1997 | Hudkins et al. |
| 5,593,884 A | 1/1997 | Karin et al. |
| 5,594,009 A | 1/1997 | Hudkins et al. |
| 5,605,808 A | 2/1997 | Karin et al. |
| 5,621,100 A | 4/1997 | Lewis et al. |
| 5,621,101 A | 4/1997 | Lewis et al. |
| 5,676,945 A | 10/1997 | Reddy et al. |
| 5,705,511 A | 1/1998 | Hudkins et al. |
| 5,741,808 A | 4/1998 | Lewis et al. |
| 5,750,555 A | 5/1998 | Trostmann et al. |
| 5,756,494 A | 5/1998 | Lewis et al. |
| 5,817,479 A | * 10/1998 | Au-Young et al. .......... 435/69.1 |
| 5,840,509 A | * 11/1998 | Ni et al. |
| 5,854,043 A | * 12/1998 | Johnson |
| 6,060,247 A | * 5/2000 | Miller et al. .................... 435/6 |
| 6,127,401 A | 10/2000 | Singh et al. |
| 6,159,948 A | 12/2000 | Robertson et al. |
| 6,455,525 B1 | 9/2002 | Singh et al. |
| 6,514,745 B1 | 2/2003 | Karin et al. |
| 2002/0028815 A1 | 3/2002 | Ator et al. |
| 2002/0061920 A1 | 5/2002 | Gingrich et al. |
| 2002/0198219 A1 | 12/2002 | Grant et al. |

FOREIGN PATENT DOCUMENTS

| | | |
|---|---|---|
| CA | 2148898 | 5/1995 |
| WO | WO 93/15201 | 8/1993 |
| WO | WO 94/17498 | 8/1994 |
| WO | WO 95/03324 | 2/1995 |
| WO | WO 95/23849 | 9/1995 |
| WO | WO 99 18193 | 4/1999 |
| WO | WO 99/58982 | 11/1999 |
| WO | WO 00/13015 | 3/2000 |
| WO | WO 00/47583 | 8/2000 |
| WO | WO 02/14536 | 2/2002 |

OTHER PUBLICATIONS

Liu et al., *Society for Neuroscience Abstracts*, 23(1–2): 1909, Oct. 1997.*
Gooderough et al., *Society for Neuroscience Abstracts*, 23(1–2):1387, Oct. 1997.*
Cheung, et al., *Journal of Neuroscience Research*, 52(1):69–82, Apr. 1998.*
Yardin et al., *Neuroreport*, 9(9):2077–80, Jun. 1998.*
Yan et al., Activation of stress–activated protein kinase by MEKK1 phosphorylation of its activator SEK1, Dec. 1994, Nature, vol. 372, pp. 798–300.*
Tibbles et al., MLK–3 activates the SAPK/JNK and p378/RK pathways via SEK1 and MKK3/6, 1996, The EMBO Journal, vol. 15, no. 24, pp. 7026–7035.*
Angeles, T. et al., Enzyme–linked Immunosorbent Assay for trkA Tyrosine Kinase Activity, Analytical Biochemistry, 236: 49–55, 1996.
Bergeron et al., Inhibition of Cell Growth by Overexpression of the ZPK Gene. Biochemical and Biophysical Research Communications, 231:153–155, 1997.
Blouin et al., Cell–Specific Expression of the ZPK Gene in Adult Mouse Tissues. DNA and Cell Biology, 15: 631–642, 1996.
Davis, R.J., Human JNK3 Alpha 2 Protein Kinase (JNK3A2) mRNA. GenBank Accession No. U34819, Jul. 25, 1996.
Davis, R.J., Human JNK3 Alpha 2 Protein Kinase (JNK3A2) mRNA. GenBank Accession No. U34820, Jul. 25, 1996.
DeAizpurua et al., Expression of Mixed Lineage Kinase–1 in Pancreatic β–Cell Lines at Different Stages of Maturation and During Embryonic Pancreas Development. The Journal of Biological Chemistry, 272:16364–16373, 1997.
Diener et al., Activation of the c–Jun N–terminal kinase pathway by a novel protein kinase related to human germinal center kinase. Proc. Natl. Acad. Sci. USA, 94:9687–9692, 1997.

(List continued on next page.)

*Primary Examiner*—Marianne P. Allen
(74) *Attorney, Agent, or Firm*—Wolf, Greenfield & Sacks, P.C.

(57) ABSTRACT

The present invention describes methods for identifying compounds that inhibit JNK and MLK kinase activity as drugs for treating a mammal susceptible to or having a neurological condition. This invention also discloses methods for preventing neuronal cell death and treating neurological conditions that involve neuronal cell death, particularly neurodegenerative diseases characterized by glutamine or kainate mediated toxicity, such as Huntington's disease and Alzheimer's disease.

13 Claims, 14 Drawing Sheets

OTHER PUBLICATIONS

Dorow et al., Identification of a new family of human epithelial protein kinases containing two leucine/isoleucine–zipper domains. Eur. J. Biochem, 213:701–710, 1993.

Ezoe et al, PTK1, a novel protein kinase required for proliferation of human melanocytes. Oncogene, 9:935–938, 1994.

Fan et al., Dual Leucine Zipper–bearing Kinase (DLK) Activates p46SAPK and p38mapk but not ERK2. Journal of Biological Chemistry, 271:24788–24793, 1996.

Fanger, G.R. et al., MEKKs, GCKs, MLKs, PAKs, TAKS, and tpls: Upstream Regulators of the c–jun Amino–Terminal Kinases! Current Opinion in Genetics and Development, 7:67–74, 1997.

Glicksman et al., CEP–1347/KT7515 Prevents Motor Neuronal Programmed Cell Death and Injury–Induced Dedifferentiation in Vivo. Journal of Neurobiology, 34: 361–370, 1998.

Glicksman et al., K–252a and Staurosporine promote Choline Acetyltransferase Activity in Rat Spinal Cord Cultures. Journal of Neurochemistry, 61:210–221, 1933.

Hambleton et al., Activation of c–Jun N–terminal kinase in bacterial lipopolysaccharide–stimulated macrophages. Proc. Natl. Acad. Sci. USA, 93: 2774–2778, 1996.

Hirai et al., Activation of the JNK pathway by distinctly related protien kinases, MEKK and MUK. Oncogene, 12:641–650, 1996.

Holzman et al., Identification, Molecular Cloning, and Characterization of Dual Leucine Zipper Bearing Kinase, Journal of Biological Chemistry, 269: 30808–30817, 1994.

Hu et al., Human HPK1, a novel human hematopoietic progenitor kinase that activates the NJK/SAPK kinase cascade. Genes and Development, 10:2251–2264, 1996.

Ing et al., MLK–3: identification of a widely–expressed protein kinase bearing an SH3 domain and a leucine zipper–basic region domain. Oncogene, 9:1745–1750, 1994.

Kaneko et al., Neurotrophic 3, 9–bis (alkylthio)methyl–and–bis(alkoxymethyl)–K–252a Derivatives. J. Med. Chem. 40:1863–1869, 1997.

Katoh et al., Cloning and Characterization of MSTK, a novel (putative) serine/threonine kinase with SH3 domain, Oncogene, 10: 1447–1451, 1995.

Kiefer et al., HPK1, a hematopoietic protein kinase activating the SAPK/JNK pathway, EMBO Journal, 15: 7013–7025, 1996.

Knight, E. et al., A Radioactive Binding Assay for Inhibitors of trkA Kinase. Analytical Biochemistry, 247:376–381, 1997.

Maroney et al., Motoncuran Apoptosis is blocked by CEP–1347 (KT 7515), a Novel Inhibitor of the JNK Signaling Pathway. Journal of Neuroscience, 18(1): 104–111, 1998.

Mata et al., Characterization of Dual Leucine Zipper–bearing Kinase, a Mixed Lineage Kinase Present in Synaptic Terminals whose Phosphorylation State is Regulated by Membrane Depolarization via Calcineurin, Journal of Biological Chemistry, 271: 16888–16896, 1996.

Nagata et al., The MAP kinase kinase kinase MLK2 co–localizes with activated JNK along microtubules and associaters with kinesin superfamily motor KIF3. EMBO Journal, 17: 149:158, 1998.

Park et al., Ordering the Cell Death Pathway, J. Biol. Chem. 271(36):21896–21905, 1996.

Phelps et al., Generation Patterns of Four Groups of Cholinergic Neurons in Rat Cervical Spinal Cord: A Combined Tritiated Thymidine Autoradiographic and Choline Acetyltransferase Immunocytochemical Study, Journal of Comparative Neurology, 272:459–472, 1998.

Pombo et al., Activation of the SAPK pathway by the human STE20 homologue germinal centre kinase. Nature, 377: 750–754, 1995.

Qin et al., Nuclear Factor–xB Contributes to Excitotoxin–Induced Apoptosis in Rat Striatum. Molecular Pharmacology, 53:33–42, 1998.

Reddy et al., Cloning of a Novel Putative Protein Kinase Having A Leucine Zipper Domain From Human Brain, Biochemical and Biophysical Research Communication, 202: 613–620, 1994.

Sakuma et al., Molecular Cloning and Functional Expression of a cDNA Encoding a New Member of Mixed Lineage Protein Kinase from Human Brain, Journal of Biological Chemistry, 272:28622–28629, 1997.

Sells et al., Emerging from the Pak: the p21–activated protein kinase family. Trends in Cell Biology, 7: 162–167, 1997.

Smith et al., Trophic Effects of Skeletal Muscle Extracts on Ventral Spinal Cord Neurons in Vitro: Separation of a Protein with Morphologic Activity from Proteins with Cholinergic Activity. Journal of Cell Biology, 101: 1608–1621, 1995.

Su et al., NIK is a new Ste20–related kinase that binds NCK and MEKK1 and activates the SAPK/JNK cascade via a conserved regulatory domain. The EMBO Journal, 16: 1279–1290, 1997.

Tung et al., A novel human SPS1/STE20 homolgoue, KHS, activates Jun N–terminal kinase. Oncogene, 14:653–659, 1997.

Liu, Ya Fang, "Expression of Polyglutamine–expanded Huntington Activates the SEK1–JNK Pathway and Induces Apoptosis in a Hippocampal Neuronal Cell Line," J. Biol. Chem., 273(44): 28873–77 (Oct. 30, 1998).

Liu, Y.F. et al., "SH3 Domain–dependent Association of Huntingtin with Epidermal Growth Factor Receptor Signaling Complexes," J. Biol. Chem. 272(13): 8121–8124 (Mar. 28, 1997).

Yang, D.D. et al., "Absence of Excitotoxicity–Induced Apoptosis in the Hippocampus of Mice Lacking the Jnk3 Gene," Nature 389: 865–870 (Oct. 23, 1997).

Dorrow, Donna S. et al., "Complete Nucleotide Sequence, Expression, and Chromsomal Localisation of Human Mixed–Lineage Kinase 2," Eur. J. Biochem., 234: 492–500 (1995).

Maroney, Anna C. et al., "Motoneuron Apoptosis is Blocked by CEP–1347 (KT 7515), a Novel Inhibitor of the JNK Signaling Pathway," J. of Neuroscience, 18(1): 104–111 (Jan. 1, 1998).

Anderson, A.J. et al., "DNA Damage and Apoptosis in Alzheimer's Disease: Colocalization with c–Jun Immunoreactivity, Relationship to Brain Area, and Effect of Postmortem Delay," J. of Neuroscience, 16(5): 1710–1719 (Mar. 1, 1996).

Eilers, A. et al., "Role of the Jun Kinase Pathway in the Regulation of c–Jun Expression and Apoptosis in Sympathetic Nuerons," J. of Neuroscience, 18(5): 1713–1724 (Mar. 1, 1998).

Liu, Z. et al., "Dissection of TNF Receptor 1 Effector Functions: JNK Activation is Not Linked to Apoptosis While NF–kB Activation Prevents Cell Death," *Cell* 87:565–576 (Nov. 1996).

Thomas, L.B. et al., "DNA End Labeling (TUNEL) in Huntington's Disease and Other Neuropathological Conditions," *Exp. Neurol.* 133(2): 265–272 (Jun. 1995) (Abstract only).

Paulson, H.L. et al., Trinucleotide Repeats in Neurogenetic Disorders, *Annu. Rev. Neurosci.* 19: 79–107 (1996).

Kyriakis, J.M. et al., "The Stress–Activated Protein Kinase Subfamily of c–Jun Kinases," *Nature* 369: 156–160 (May 12, 1994).

The Huntington's Disease Collective Research Group, "A Novel Gene Containing a Trinucleotide Repeat that is Expanded and Unstable on Huntington's Disease Chromosomes," *Cell,* 72: 971–983 (Mar. 26, 1993).

Martin, J.H. et al., "Developmental Expression in the Mouse Nervous System of the p493F12 SAP Kinase," *Brain Res. Mol. Brain Res.,* 35(1–2): 47–57 (Jan. 1996) (Abstract only).

Snell, R. et al., "Relationship Between Trinucleotide Repeat Expansion and Phenotypic Variation in Huntington's Disease," *Nature Genetics, 4:* 393–397 (Aug. 1993).

Virdee, K. et al., "Composition Between the Timing of JNK Activation, c–Jun Phosphorylation, and Onset of Death Commitment in Sympathetic Neurones," *J. Neurochem.,* 69(2): 550–561 ((1997).

Gupta, S. et al., "Selective Interaction of JNK Protein Kinase Isoforms with Transcription Factors," *EMBO J.,* 15(11): 2760–2770 (1996).

Nishina, H. et al., "Stress–Signalling Kinase Sekl Protects Thymocytes from Apoptosis Mediated by CD95 and CD3," *Nature* 385: 350–357 (Jan. 23, 1997).

Derijard, B. et al., "JNK1: A Protein Kinase Stimulated by UV Light and Ha–Ras That Binds and Phosphorylates the c–Jun Activation Domain," *Cell* 76: 1025–1037 (Mar. 25, 1994).

Ham, J. et al., "A c–Jun Dominant Negative Mutant Protects Sympathetic Neurons against Programmed Cell Death," *Neuron,* 14: 927–939 (May 1995).

Hirai, S. et al., "MST/MLK2, a Member of the Mixed Lineage Kinase Family, Directly Phosphorylates and Activates SEK1, an Activator of c–Jun N–terminal Kinase/Stress–activated Protein Kinase," *J. Biol. Chem.* 272(24): 15167–15173 (Jun. 13, 1997).

Schwarzschild, M.A. et al., "Glutamate, But Not Dopamine, Stimulates Stress–Activated Protein Kinase and AP–1–Mediate Transcription in Striatal Neurons," *J. of Neurosci.* 17(10): 3455–3466 (May 15, 1997).

Herdegen, T. et al., "Lasting N–Terminal Phosphorylation of c–Jun and Activation of c–Jun N–Terminal Kinase after Neuronal Injury," *J. of Neurosci.* 18(14: 5124–5135 (Jul. 15, 1998).

Lin, A. et al., "Identification of a Dual Specificity Kinase that Activates the Jun Kinases and p38–Mpk2," *Science* 268: 286–290 (Apr. 14, 1995).

Nagafuchi, S. et al., "Structure and Expression of the Gene Responsible for the Triplet Repeat Disorder, Dentatorubral and Pallidoluysian Atrophy (DRPLA)," *Nature Genetics* 8: 177–182 (Oct. 1994).

Gallo, K.A. et al., "Identification and Characterization of SPRK, a Novel, src–Homology 3 Domain–containing Proline–rich Kinase with Serine/Threonine Kinase Activity," *J. of Biol. Chem.* 269(21): 15092–15100 (May 27, 1994).

Rana, A. et al., "The Mixed Lineage Kinase SPRK Phosphorylates and Activates the Stress–activated Protein Kinase Activation, SEK–1," *J. Biol. Chem.* 271(32): 19025–19028 (Aug. 9, 1996).

David, G. et al., "Cloning of the SCA7 Gene Reveals a Highly Unstable CAG Repeat Expansion," *Nature Genetics* 17: 65–70 (Sep. 1997).

Bossy–Wetzel, E. et al., "Induction of Apoptosis by the Transcription Factor c–Jun," *EMBO J.* 16(7): 1695–1709 ((1997).

Chen, Y. et al., "The Role of c–Jun N–terminal Kinase (JNK) in Apoptosis Induced by Ultraviolet C and Y Radiation," *J. Biol. Chem.* 271(50): 31929–31936 (Dec. 13, 1996).

Duyao, M. et al., "Trinucloetide Repeat Length Instability and Age of Onset in Huntington's Disease," *Nature Genetics* 4: 387–392 (Aug. 1993).

Davis, R.J., "MAPKs: New JNK Expands the Group," *TIBS* 19: 470–473 (Nov. 1994).

Davis, R.J., "Human JNK3 Alpha 2 Protein Kinase (JNK3A2) mRNA," GenBank Assession No. U33819.

Davis, R.J., "Human JNK3 Alpha 2 Protein Kinase (JNK3A1) mRNA," GenBank Assession No. U33820.

M. Dickens et al., "A Cytoplasmic Inhibitor of JNK Signal Transduction Pathway," *Science* 277: 693–693 (Aug. 1, 1997).

* cited by examiner

METHOD FOR IDENTIFYING MLK INHIBITORS FOR THE TREATMENT OF NEUROLOGICAL CONDITIONS

RELATED APPLICATION

This application claims the benefit of U.S. Provisional Application Ser. No. 60/085,439, filed May 14, 1998, the entire teachings of which are incorporated herein by reference.

BACKGROUND OF THE INVENTION

Excitotoxicity is related to excessive activation of glutamate receptors which results in neuronal cell death. The physiological function of glutamate receptors is the mediation of ligand-gated cation channels with the concomitant influx of calcium, sodium and potassium through this receptor-gated channel. The influx of these cations is essential for maintaining membrane potentials and the plasticity of neurons which in itself plays a pivotal role in cognitive function of the central nervous system. Li, H. B., et al., *Behav. Brain Res.*, 83:225–228 (1997); Roesler, R., et al., *Neurology*, 50:1195 (1998); Wheal, H. V., et al., *Prog. Neurobiol.*, 55:611–640 (1998); Wangen, K., et al., *Brain Res.*, 99:126–130 (1997). Excitotoxicity plays an important role in neuronal cell death following acute insults such as hypoxia, ischemia, stroke and trauna, and it also plays a significant role in neuronal loss in AIDS dementia, epilepsy, focal ischemia. Coyle, J. T. & Puttfarken, P., *Science*, 262:689–695 (1993). Neurodegenerative disorders, such as Huntington's disease (HD), Alzheimer's disease (AD), Parkinson's disease (PD) and amyotrophic lateral sclerosis (ALS), are characterized by the progressive loss of a specific population of neurons in the central nervous system. Growing evidence suggests that glutamate-mediated excitotoxicity may be a common pathway which contributes to neuronal cell death in a wide range of neurological disorders. Coyle, J. T. & Puttfarken, P., *Science*, 262:689–695 (1993).

The molecular mechanisms of excitotoxicity-mediated neuronal cell death remains obscure. Over-production of free radicals that lead to impairment of mitochondrial function is the most widely held hypothesis. Beal, M. F., et al., *Ann. Neurol.*, 38:357–366 (1995); Coyle, J. T. & Puttfarken, P., *Science*, 262:689–695 (1993) However, it is unclear whether the increase of free radicals is the precursor that initiates neuronal degeneration or, rather, a subsequent consequence of neuronal degeneration. Interestingly, administration of antioxidants has little neuroprotective effect in patients suffering from various neurodegenerative diseases. Shults, C. W., et al., *Neurology*, 50:793–795 (1998). Thus, some other mechanism(s) must exist for excitotoxicity-induced neuronal cell death.

c-Jun N-terminal kinases (JNKs) are identified as kinases which are activated upon stimulation by various environmental stimuli such as UV light, λ irradiation and mitogenic signals. Hibi, M., et al., *Genes Dev.*, 7:2135–2148 (1993); Kyriakis, J. M., et al., *Nature*, 369:156–160 (1994). The precise biological function of JNKs remains to be explored. However, some recent reports suggest that JNKs are involved in neuronal apoptosis induced by deprivation of survival factors, i.e., neurotrophic factors which support neuronal survival. Ham, J., et al., *Neuron*, 14:927–939 (1995).

Mixed-lineage kinases (MLKs), so called because these proteins contain structural domains associated with a variety of cell types, were cloned from a cDNA library derived from mRNA from cancer tissue. MLKs were initially thought to participate in the oncogenesis of some cancers, although high levels of expression of MLKs were found in the normal brain. Dorow, D. S., et al., *Eur. J. Biochem.*, 213:701–710 (1993); Dorow, D. S., et al., *Eur. J. Biochem.*, 234:492–500 (1995).

Searching for biochemical targets which are amenable to screening for neuroprotective therapeutic agents is of central concern in neuroscience today. However, no clinically available pharmaceutical tool to date is employed for blocking excitotoxicity and preventing neuronal cell loss in various neurological disorders due to a lack of suitable biochemical targets. Glutamate receptor antagonists, such as MK-801, although successful in protecting neurons in animal experiments, have all failed in the clinical setting due to their blockage of cognitive function mediated by the receptors, as well as high toxicity to the central nervous system. Thus, an understanding of the molecular mechanism(s) of neuronal cell death induced by excitotoxicity is essential for the identification of new biochemical targets and the establishment of reliable methods for screening new therapeutic drugs from chemical libraries that can be utilized in the treatment of a variety of neurological disorders.

SUMMARY OF THE INVENTION

This invention relates to the discovery that inhibiting a JNK or MLK within a hippocampal neuronal cell can protect the cell from apoptosis. As such, JNK and MLK can be used as drug targets to screen for therapeutic agents to prevent glutamate or kainic acid mediated toxicity, to block excitotoxicity and to prevent neuronal loss in a variety of neurological conditions, such as Huntington's disease and Alzheimer's disease.

In one aspect of the invention, a method is described for assessing a compound's ability to inhibit neuronal cell death, and thus to identify compounds that can be used to prevent and/or treat neurological conditions. According to the method, neuronal cells having activated MLK and/or JNK activity are contacted with a compound and the number of neuronal cells that die is determined. A decrease in the number of dead neuronal cells in the presence of the compound compared to the number of dead neuronal cells in the absence of the compound is indicative of the compound's ability to inhibit neuronal cell death. Preferably, the neuronal cells are apoptotic neurons (i.e., cell death caused by a neurological condition) or neurons that are induced to undergo apoptosis, such as by contacting the neuronal cells with neurotoxin (e.g., glutamate, quinolinic acid or kainic acid); or by genetic manipulation of the neuronal cells. Most preferred are HN33 hippocampal neuronal cells.

In another embodiment, the invention features a method for testing a compound's potential as a drug for treating a mammal (e.g., a human) susceptible to or having a neurological condition by (1) contacting a compound with a JNK (e.g., JNK3) or MLK (e.g., MLK2); (2) measuring the level of a JNK-associated or MLK-associated activity (e.g., a kinase activity); and (3) comparing the level of the JNK-associated or MLK-associated activity in the presence of the compound with the level of the JNK-associated or MLK-associated activity in the absence of the compound. The compound is a potentially useful drug for treating the mammal when the level of the JNK-associated or MLK-associated activity in the presence of the compound is less than the level of the JNK-associated or MLK-associated activity in the absence of the compound.

The JNK or MLK can be within a cell, which can be an animal (e.g., human) cell in vivo. When the JNK or MLK is within a cell, the JNK-associated or MLK-associated activity can be apoptosis, which can be measured by a TUNEL assay (described below). Apoptosis within such a cell can be induced by introducing into the cell a huntingtin protein that has at least 40 consecutive glutarnic acids (e.g., polyglutamine stretch-expanded huntingtin). Alternatively, apoptosis can be induced by introducing into the cell the C-terminal 100 amino acids of an amyloid precursor protein (APP). Preferably, the huntingtin protein or the amyloid precursor protein is introduced by a vector, especially a nucleic acid vector. When the cell is within an animal, the JNK-associated or MLK-associated activity can be neurodegeneration.

The invention also features a method for testing a compound's potential as a drug for treating a mammal (e.g., a human) susceptible to or having a neurological condition by (1) contacting a compound with a neuronal cell containing a JNK (e.g., JNK3) or MLK (e.g., MLK2); (2) measuring the level of a JNK or MLK protein activity (e.g., kinase activity, such as the presence or amount of phosphorylated product) in the cell; and (3) comparing the level of the INK or MLK protein activity in the cell in the presence of the compound with the level of the JNK or MLK protein activity in the cell in the absence of the compound. The compound is a potentially useful drug for treating the mammal when the level of the JNK or MLK protein activity in the cell in the presence of the compound is less than the level of the JNK or MLK protein activity in the cell in the absence of the compound. Alternatively, cell viability can be ascertained by determining the degree of neuronal cell death, wherein a decreased number of dead neuronal cells in the presence of the compound compared to the number of dead neuronal cells in the absence of the compound is indicative of the compound's ability to inhibit JNK or MLK protein activity, thereby preventing neuronal cell death.

In another aspect, the invention provides a method for testing the potential of a JNK or MLK inhibitor as a drug for treating a mammal (e.g., a human) susceptible to or having a neurological condition. The method can be performed on compounds identified as JNK and/or MLK inhibitory agents using the methods of this invention to confirm their inhibitory effectiveness under apoptotic conditions. Accordingly, the method provides (1) incubating a neuronal cell in the presence of a JNK or MLK inhibitor; (2) contacting surviving cells with an agent that induces apoptosis in the cell; and (3) comparing the occurrence of apoptosis in the cell in the presence of the JNK or MLK inhibitor with the occurrence of apoptosis in the cell in the absence of the JNK or MLK inhibitor. The compound is a potentially useful drug for treating the mammal when the occurrence of apoptosis in the cell in the presence of the JNK or MLK inhibitor is less than the occurrence of apoptosis in the cell in the absence of the JNK or MLK inhibitor.

The methods of the invention are used to identify inhibitors of JNK or MLK which are potentially useful for the treatment of a neurological condition, including neuronal cell death following acute insults such as hypoxia, ischemia, stroke, and trauma. Other neurological conditions treatable with compounds identified by the methods of the invention include AIDS dementia, epilepsy, focal ischemia, Huntington's disease, Alzheimer's disease, Parkinson's disease, and amyotrophic lateral sclerosis. Each of these conditions are characterized by the progressive loss of a specific population of neurons in the central nervous system. The methods of the invention are particularly useful in finding compounds which can be used to prevent and/or treat neurological conditions, including genetic neurological conditions. The invention also pertains to compounds, identified using the methods described herein, that inhibit MLK and/or JNK activity and that prevent neuronal cell death occurring in a mammal susceptible to or having a neurological condition, particularly neurodegenerative diseases, such as Huntington's disease and Alzheimer's disease.

The invention also provides methods for preventing and/or treating neuronal conditions in a mammal comprising administering to a mammal, in need thereof, an effective therapeutic amount of a compound that inhibits JNK and/or MLK. The inhibitory effects of the compound will reduce and/or prevent neuron cell death occurring in a mammal susceptible to or having a neurological condition. In a preferred embodiment, the neurological condition is a neurological disease whereby glutamate or kainic acid mediated excitotoxicity is involved in neuronal cell death. JNK and/or MLK inhibitors identified using any of the methods described herein are useful as therapeutic or prophylatic drugs to prevent neuronal loss.

DETAILED DESCRIPTION OF THE INVENTION

Figure 1:
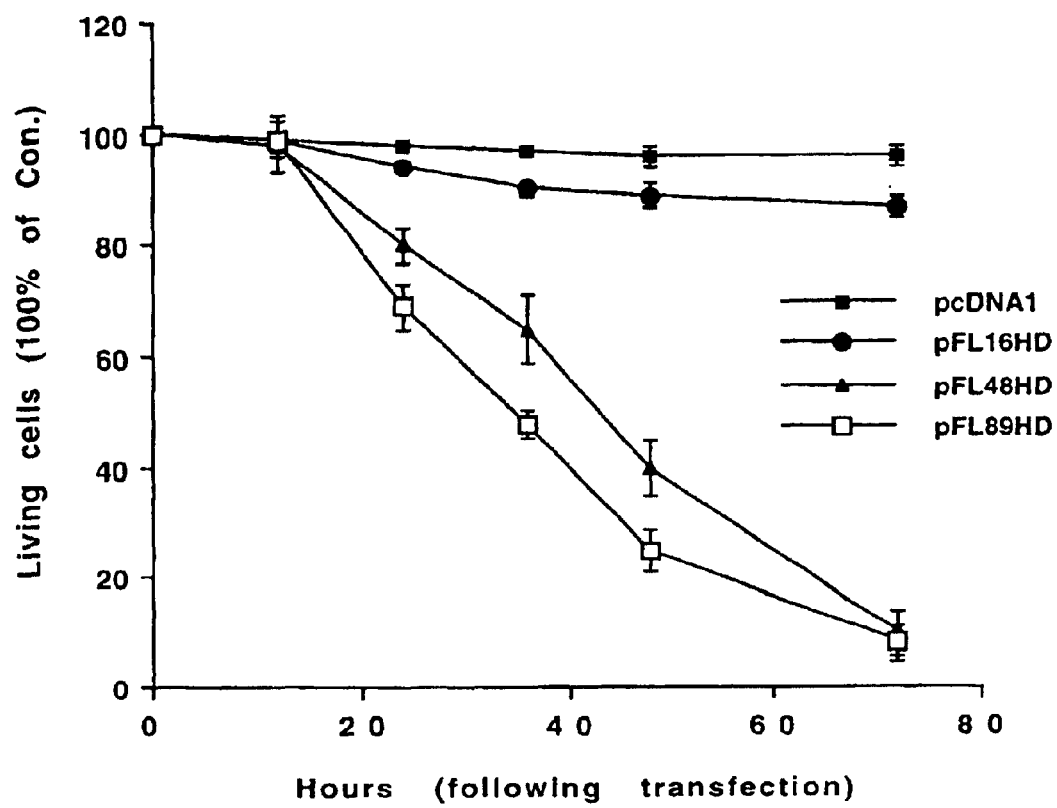
FIG. 1 is a graph illustrating a time course of cell death upon expression of normal or mutated huntingtin in HN33 cells. pcDNA1 (solid box), pFL16HD (circles), pFL48HD (triangles) and pFL89HG (open boxes).

The invention relates to the discovery that two families of proteins, JNK and MLK, can serve as targets for the treatment of neurological conditions. It has been discovered that inhibition of JNK3, a member of the JNK family, and MLK2, a member of the MLK family, can protect a neuronal cell from apoptosis induced by polyglutamine-expanded huntingtin, whose expression caused HD in humans. The Huntington's Disease Collaborative Research Group, *Cell*, 72:971–983 (1993). Thus, the invention provides a method for assessing compounds for their potential as drugs for the treatment of neurological conditions, such as Huntington's disease, by determining whether the compound can inhibit a JNK- or MLK-associated activity.

MLK and JNK participate in a biochemical cascade (activation of MLK-SEK1-JNK1) that mediates neuronal cell toxicity. Upon stimulation by glutamate, kainic acid, or other receptor agonists, the glutamate receptor, located at the cell surface, is activated and interacts with associated proteins (e.g., PDZ domain-containing proteins) whose SH3 domain in turn binds to a MLK protein, thereby activating its kinase activity. The MLK protein directly binds to and stimulates a SEK1 protein which in turn binds to and stimulates JNK. Over stimulation of JNK can lead to neuronal apoptosis (cell death). Normally MLK is inhibited by a protein, such as normal huntingtin, binding to its SH3 domain thus inhibiting the enzyme's kinase activity. This inhibition prevents the formation of the cascade resulting in no or little JNK activity, thereby preserving neuronal cell viability.

To determine whether polyglutamine-expanded huntingtin induced cell toxicity in neurons, the expression of huntingtins with 16, 48 or 89 CAG repeats in an immortalized rat hippocampal neuronal cell line (HN33) was examined. HN33 has been described in detail in Hammond, D. N., et al., *Brain Res.*, 512:190–200 (1990); the entire teachings of which are incorporated herein by reference. The hippocampal neurons serve as a potential target of mutated huntingtin, mutated amyloid precursor protein (APP), as well as glutamate stimulation. The results demonstrated that expression of mutated huntingtin with 48 or 89 CAG repeats stimulated JNKs and induced apoptotic cell death in HN33 cells, while expression of normal huntingtin with 16 CAG repeats had no toxic effect. JNK activation occurs several hours prior to neuronal apoptosis suggesting that it is an early signal for the induction of neuronal apoptosis. Furthermore, co-expression of a dominant negative form of stress signaling kinase (SEK1), which serve as a specific inhibitor of JNKs, attenuated both JNK activation and neuronal apoptosis induced by mutated huntingtin. This study demonstrates that JNK activation can mediate neuronal cell death in neurological disorders. Like mutated huntingtin, the treatment of HN33 cells with glutamate also resulted in JNK activation and apoptotic cell death. Expression of dominant negative mutant SEK1 significantly attenuated glutamate-induced toxicity. Taken together, these studies indicate that JNK is a common cellular mediator for induction of neuronal cell death mediated by both glutamate and mutated huntingtin.

The mechanism for how mutated huntingtin stimulates JNKs was also examined. The huntingtin protein contains multiple SH3 domain binding sites. In previous studies, it has been demonstrated that normal huntingtin directly binds to SH3domain-containing proteins Grb2 and RasGAP. Liu, Y. F., et aL, *J. Biol. Chem.*, 272:8121–8124 (1997). MLKI, MLK2 and MLK3 (MLKs) are the only known kinases that directly activate the SEKI-JNK cascade and contain a SH3 domain as well as a SH3 domain binding site. MLK2 is a neuronal form of MLKs. The presence of MLKs, in particular MLK2, appears to be required for mutated huntingtin-mediated JNK activation and neuronal apoptosis. MLKs were expressed in HN33 cells where expression of mutated huntingtin induced JNK activation and apoptosis, while in both 293 and CHO cells where MLKs are absent, the expression of mutated huntingtin did not generate any cell toxicity in 293 and CHO cells. However, co-expression of mutated huntingtin along with MLK2 in 293 cells caused rapid apoptotic cell death. The SH3 domain of MLKs is required for their proper cellular localization and activation of the SEK1-JNK pathway. In the in vitro binding studies, it was shown that normal huntingtin binds to the SH3 domain of MLK2 and inhibits enzyme activity while expansion of the polyglutamine repeats interferes with huntingtin's binding and consequently is not inhibitory with respect to MLK2's activity. Furthermore, expression of kinase dead MLK2 completely blocks mutated huntingtin-induced neuronal cell death. These studies indicate that mutation of huntingtin results in an increase of free MLKs thereby causing over-activation of the MLK-SEK1-JNK cascade which ultimately leads to neuronal cell death.

The SH3 binding motif is found in six other proteins involved in polyglutamine repeat-expanded neurodegenerative hereditary diseases, such as ataxia-1, ataxia-2, ataxia-6, ataxia-7, Kennedy disease, dentatorubral and pallidoluysian atrophy (DRPLA). The normal (wild-type) counter-part proteins bind to and suppress MLK activity, in contrast to the mutated protein form which lose such ability, resulting in the over-activation of the MLK2-SEK1-JNK pathway in neurons.

The JNK kinases phosphorylate and activate the transcription factor c-Jun which mediates apoptosis. Recent studies suggest that c-Jun may serve as an important mediator for neuronal apoptosis induced by a variety of environmental stresses. In primary cultured sympathetic, hippocampal or cerebellar granule neurons, deprivation of growth factor in these primary cultures lead to persistent activation of JNKs and consequently the phosphorylation of c-Jun. Ham, J., et al., *Neuron*, 14:927–939 (1995); Xia, Z., et al, *Science*, 270:1326–1330 (1995). Suppression of c-Jun expression by antisense-oligonucleotides, or functional blockade by microinjection of antibodies or expression of dominant negative c-Jun prevents neuronal apoptosis; in contrast, over-expression of c-Jun induces apoptosis in sympathetic neurons. Estus, S., et al., *J. Cell Biol.*, 127:1717–1727 (1994); Ham, J., et al., *Neuron*, 14:927–939 (1995). Enhanced c-Jun expression occurs in degenerating and apoptotic neurons after ischemia, nerve fiber transection, axotomized brains, UV irradiation and various other types of neuronal injury. Ferrer, I., et al., *Eur. J. Neurosci.*, 8:1286–1298(1998); Herdegen, T., et al., *J. Neurosci.*, 18:5124–5135 (1998).

Increased c-Jun expression and activation are also implicated in the generation of the neuronal apoptotic process induced by glutamate or kainic acid. Administration of glutamate or quinolinic acid, a N-methyl-D-aspartate (NMDA) receptor agonist, or kainic acid in rats results in a rapid induction of c-Jun expression and neuronal apoptosis. Coyle, J. T. & Puttfarken, P., *Science*, 262:689–695 (1993); Qin, Z.-H., et al., *Mol. Pharmacol.*, 53:33–42 (1997). These physiological events can be blocked by the NMDA receptor antagonist MK-801. Qin, Z.-H., el al., *Mol. Pharmacol.*, 53:33–42 (1997).

Over-activation of the c-Jun-mediated JNK cascade has also been implicated in various other neurodegenerative disorders. Enhanced c-Jun expression is observed in the brains from patients suffering from multiple sclerosis, AD and ALS. Anderson, A. J., et al., *Exp. Neurol*, 125:286–295 (1994); Martin, D. G., et al., *Neurosci. Lett.*, 212:95–98 (1996). These studies support the basis of the present invention in that the over-activation (or stimulation) of the MLK-SEK1-JNK cascade leads to the increase of expression, activation and translocation of c-Jun which is responsible for neuronal cell death in these, and other, neurodegenerative disorders. Thus, inhibition of this cascade can protect neurons from toxicity induced by endo- and/or exo-toxins including, but not limited to, mutated proteins like huntingtin, quinolinic acid, kainic acid, glutamate over-excitation as well as other etiological agents.

Based upon these findings, JNK and MLK can be used as targets for the development of inhibitory compounds of JNK- and MLK-associated activity, and such compounds can be used to prevent neuronal loss, such as induced by excitotoxicity or glutamate- or kainic acid-mediated toxicity. As used herein, a "JNK-associated activity" is any biochemical, cellular, or physiological property that varies with any variation in JNK gene transcription or translation, or JNK protein activity. Likewise, a "MLK-associated activity" is any biochemical, cellular, or physiological property that varies with any variation in MLK gene transcription or translation, or MLK protein activity. A JNK or MLK inhibitor is a compound that inhibits a JNK or MLK protein activity. A JNK or MLK protein activity is any measurable biochemical activity possessed by the protein, e.g., a kinase activity or an ability to bind to another protein such as c-Jun.

Inhibitors of MLKs identified by the methods described herein can block persistent activation of glutamate receptor-induced over-activation of MLKs without affecting other receptor functions, such as the involvement of neuronal plasticity and cognitive functions. Inhibition of MLKs will attenuate the JNK activity in neurons and protect neurons from excitotoxicity thereby preventing neuronal loss in these diseases. Inhibitors of JNKs or MLKs identified by the methods described herein can suppress glutamate receptor-induced activation of the MLK-SEK1-JNK cascade and prevent neuronal apoptosis in various neurological diseases.

The term "neurological condition" as used herein is intended to embrace disorders, disease states and disturbances which cause or result in neuronal cell injury, compromise or cell death. Neurological conditions can result from axonal degeneration, ischemia due to stroke, heart arrest, exposure, exposure to neurotoxins such as, but not limited to, glutamate, kainic acid and quinolinic acid, MPTP exposure to bacterial or viral toxins, impaired function or dysfunction of neurons such as increase or decrease of neurotransmitter synthesis andlor release. Neurological diseases and disturbances include, but are not limited to, Alzheimer's disease; Parkinson's disease; motor neuron diseases such as amyotrophic lateral sclerosis (ALS), Huntington's disease and syringomyelia; ataxias, dementias; chorea; dystonia; dyslinesia; encephalomyelopathy; parenchymatous cerebellar degeneration; Kennedy disease; Down syndrome; progressive supernuclear palsy; DRPLA, stroke or other ischemic injuries; thoracic outlet syndrome, trauma; electrical brain injuries; decompression brain injuries; AIDS dementia; multiple sclerosis; epilepsy; concussive or penetrating injuries of the brain or spinal cord; peripheral neuropathy; brain injuries due to exposure of military hazards such as blast over-pressure, ionizing radiation, and genetic neurological conditions. By "genetic neurological condition" is meant a neurological condition, or a predisposition to it, that is caused at least in part by or correlated with a specific gene or mutation within that gene; for example, a genetic neurological condition can be caused by or correlated with more than one specific gene. Examples of genetic neurological conditions include, but are not limited to, Alzheimer's disease, Huntington's disease, spinal and bulbar muscular atrophy, fragile X syndrome, FRAXE mental retardation, myotonic dystrophy, spinocerebellar ataxia type 1, dentatorubral-pallidoluysian atrophy, and Machado-Joseph disease.

In one aspect of the invention, a method is described for assessing a compound's ability to inhibit neuronal cell death. According to the method, neuronal cells having activated MLK and/or JNK activity are contacted with a compound and the number of neuronal cells that die is determined. A decrease in the number of dead neuronal cells in the presence of the compound compared to the number of dead neuronal cells in the absence of the compound is indicative of the compound's ability to inhibit neuronal cell death. Preferably, the neuronal cells are apoptotic neurons or neurons that are induced to undergo apoptosis neuronal cells with neurotoxin or genetic manipulation.

A neuronal cell useful in the methods of the invention is preferably susceptible to JNK-dependent or MLK-dependent apoptosis. To facilitate apoptosis, such a cell can express a polypeptide known to be associated with or induce a neurodegenerative disease, such as a polyglutamine-expanded polypeptide (e.g., polyglutamine-expanded huntingtin) or the C-terminal 100 amino acid fragment of an amyloid precursor protein. A preferred neuronal cell that is useful for assessing MLK and/or JNK inhibitors is an immortalized rat hippocampal neuronal cell line HN33, with or without genetic manipulations to induce apoptosis, as described above.

In another embodiment, the invention features a method for testing a compound's potential as a drug for treating a mammal (e.g., a human) susceptible to or having a neurological condition by (1) contacting a compound with a JNK (e.g., JNK3) or MLK (e.g., MLK2); (2) measuring the level of a JNK-associated or MLK-associated activity (e.g., a kinase activity); and (3) comparing the level of the JNK-associated or MLK-associated activity in the presence of the compound with the level of the JNK-associated or MLK-associated activity in the absence of the compound. The compound is a potentially useful drug for treating the mammal when the level of the JNK-associated or MLK-associated activity in the presence of the compound is less than the level of the JNK-associated or MLK-associated activity in the absence of the compound.

In another aspect of the invention, a putative inhibitory agent is incubated in vitro in the presence of JNK and appropriate JNK substrates, such as c-Jun and a phosphate donor like adenosine triphosphate (ATP), under conditions sufficient for enzymatic activity; followed by isolating the phosphorylated product. Isolated JNK protein, including JNK1, JNK2 and JNK3, can be obtained for this, as well as other assays, by several different molecular and chromatographic methods known to those skilled in the art. The JNK polypeptides useful in the methods of the present invention are preferably wild-type whose sequence is known and readily available. The human JNK3polypeptide is described by Martin et al., Mol. Brain Res., 35:47–57 (1996). Other JNK proteins useful in the methods of the invention include those described in GenBank Accession Nos. U17743, U49249 and AF006689. Isolated JNK protein, from about 0.5 µg to about 2 µg of purified JNK, is incubated with substrate in an aqueous medium, such as a kinase buffer (containing about: 20 mM HEPES, pH 7.5, 15 mM $MgCl_2$, 15 mM β-glycerophosphate, 0.1 mM $Na_2PO_4$ and 2 mM dithiothreitol) at about 30° C. for approximately 15 minutes. The substrates that can be used in this reaction include, but are not limited to, c-Jun, from about 1 µg to about 3 µg, a known substrate for JNK's kinase activity, and the phosphate donor, ATP (approximately 2.5 mM). For detection purposes, 5 µCi of [γ-$^{32}$P]ATP can be used as a co-substrate. The assay system can also include in the incubation mixture a putative inhibitory JNK agent. The reaction can be terminated by addition of Laemmeli buffer, approximately 20 µL. The addition of this buffer will also prepare the sample for product analysis. The reaction mixture can be subjected to sodium dodecylsulfate polyacrylamide gel electrophoresis (hereinafter SDS-PAGE) in order to determine the amount of phosphorylated c-Jun that was formed in the reaction. The radioactivity emitted from the $γ^{32}P$ can be measured using conventional radioactivity gel detection systems, such as an X-ray followed by β-scan. The phosphorylated c-Jun product will have a different migration rate along the gel when compared to the labeled ATP co-substrate and therefore will not be confused with the kinase product. A determination can then be made concerning whether the test agent inhibited JNK's activity by comparing reaction mixtures having the agent present to reaction mixtures without addition of the compound.

Alternatively, JNK substrates, such as c-Jun and ATP, can be incubated in the presence of a cellular extract containing putative JNK enzyme activity, including JNK1, JNK2 and JNK3. An inhibitory agent to be tested can be placed in the reaction vial along with the other reactants to examine the efficacy of the agent. The reaction and detection protocol can be conducted in the same manner as that describe above for the in vitro assay without cellular extract. The cellular extract can originate from a cell or tissue culture system, or can be prepared from whole tissue employing isolation and purification protocols known to those skilled in the art.

In another embodiment, the invention pertains to contacting a cell with a putative inhibitory agent in order to screen for inhibitory agents of JNK activity, including JNK1, JNK2 and JNK3. The cell to be contacted can be of a cell or tissue culture system. The putative inhibitory agent is delivered to the cell under conditions sufficient for enzymatic activity in any of a number of ways known to those skilled in the art. If the agent is not membrane permeable, then the agent can be delivered into the cell via electroporation, or if it is a polypeptide, a nucleic acid or viral vector can be employed. If the cell has JNK activity present in an active form, then JNK can be stimulated by delivering to the cell SEK1, a known stimulator of JNK. If the cell lacks a JNK gene or functional JNK gene or transcript or translational product, the cell can be transfected with an operatively linked JNK gene. "Operatively linked" is intended to mean that the nucleotide sequence is linked to a regulatory sequence in a manner which allows expression of the nucleic acid sequence.

To detect the phosphorylated product, any number of protocols known to those skilled in the art can be used including, but not limited to, Western blot analysis and apoptosis analysis. Antibodies, both monoclonal and polyclonal, can be made against epitopes derived from the site on the JNK substrate bound to a phosphate group. A SDS-PAGE procedure can be performed on homogenized cell extract and subsequently subjected to Western blot analysis using an antibody specific for a phosphorylated JNK substrate, such as c-Jun.

An apoptosis analysis can also be performed in order to determine what effect, if any, the putative inhibitory agent has on JNK-associated activity. For example, an expression vector encoding JNK3 is transfected into an appropriate target cell to induce apoptosis. Target cells are cells that are susceptible to apoptosis. Rat hippocampal neuronal cell line HN33 is a preferred target cell. Alternatively, target cells which naturally contain JNK can be used. In either event, the target cells are cultured in the presence or absence of a test agent and the occurrence of apoptosis determined using known techniques. For example, staining the cell with Hoechst 3342 (Sigma Chemical Co.) and observing the stained cell under the microscope. Apoptotic cells appear containing clearly segmented, condensed chromatin. Alternatively, apoptosis can be determined by using the TUNEL assay as described by Thomas, L. B., et al., Exp. Neurol., 133:265–272 (1995). See also U.S. Pat. No. 5,593, 879, for techniques for examples of stains used to distinguish apoptotic cells.

In another embodiment, the invention pertains to a method for screening potential inhibitory agents of JNK activity, including JNK1, JNK2 and JNK3, by administering to an animal, including mammals, the agent and determining what effect, if any, the agent has on the animal's physiological status. The animal is given an amount of test agent sufficient to allow for proper pharmacodynamic absorption and tissue distribution in the animal. Preferably, the animal used is an example of a model system mimicking a neurological condition. However, to test the safety of the putative agent, a normal animal is preferably also subjected to the treatment. Following administration of the agent, the animal can be sacrificed and tissue sections from the brain, as well as other tissues, can be harvested and examined for apoptosis using, for example, the TUNEL assay. Yang, D. D., et al., Nature, 389:865–870 (1997). In another embodiment, an animal model afflicted with a neurological condition (e.g., neurodegenerative disorder) can be administered a JNK and/or MLK inhibitor and the symptoms associated with the neurological condition are evaluated. Attenuation, amelioration or improvement of the neurodegenerative symptoms can be assessed, whereby improvement is indicative of the inhibitors ability to prevent and/or treat the neurological condition.

The methods described above can be likewise employed to identify/screen for inhibitory agents of MLK-associated activity, including MLK1, MLK2 and MLK3. Appropriate MLK substrates include, but are not limited to, ATP and SEK1, a protein known to activate JNKs by phosphorylation. The MLK polypeptides useful in the methods of the present invention are preferably wild-type whose sequence is known and readily available. The human MLK2 polypeptide is described by Dorow, D. S., et al., *Eur. J. Biochem.*, 234:491–500 (1995). Another MLK protein useful in the methods of the invention is described in GenBank Accession No. L32976.

The JNK and MLK useful in the methods of the invention are not limited to the naturally occurring sequences described above. JNK and MLK containing substitutions, deletions, or additions can also be used, provided that those polypeptides retain at least one activity associated with the naturally occurring polypeptide and are at least 70% identical to the naturally occurring sequence.

To determine the percent identity of two polypeptide sequences, the sequences are aligned for optimal comparison purposes (e.g., gaps can be introduced in the sequence of a first amino acid sequence). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=# of identical positions/total # of positions×100).

The determination of percent homology between two sequences can be accomplished using a mathematical algorithm. A preferred, non-limiting example of a mathematical algorithm utilized for the comparison of two sequences is the algorithm of Karlin et al., *Proc. Natl. Acad. Sci. USA*, 90:5873–5877 (1993). Such an algorithm is incorporated into the NBLAST and XBLAST program, score=50, wordlength=3 to obtain amino acid sequence homologous to protein molecules useful in the methods of the invention. To obtain gapped alignments for comparison purposes, Gapped BLAST can be utilized as described in Altschul et al., *Nucleic Acids Res*, 25:3389–3402 (1997). When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers et al., CABIOS (1989). Such an algorithm is incorporated into the ALIGN program (version 2.0) which is part of the GCG sequence alignment software package. When utilizing the ALIGN program for comparing amino acid sequences, a PAM120weight residue table, a gap length penalty of 12, and a gap penalty of 4 can be used.

The percent of identity between two sequences can be determined using techniques similar to those described above, with or without allowing gaps. In calculating percent identity, only exact matches are counted.

An example of a JNK or MLK that is not naturally occurring, though useful in the methods of the invention, is a JNK-gluthathione-S-transferase (JNK-GST) fusion protein. Such a protein can be produced in large quantities in bacteria and isolated. The JNK fusion protein can then be used in an in vitro kinase assay in the presence or absence of a candidate drug for treating neurological conditions.

The present invention also pertains to methods for testing the effectiveness of inhibitory compound identified using the methods of this invention for neuronal protection for the prevention and/or treatment of a variety of neurological disorders. In one embodiment of the invention, the effectiveness of neuronal protection by JNK or MLK inhibitors against excitotoxicity stimuli can be assessed by the pretreatment of HN33 cells with the identified JNK or MLK inhibitors prior to stimulation with glutamate, or other neurotoxins such as kainic acid, MPP, quinolinic acid or transfection of the mutated form of huntingtin or amyloid precursor protein (APP). For example, HN33cells, plated on a 96-well plate, are grown in DMEM-F12 medium and prior to experimentation, the medium is removed and cells are washed once with serum-free medium. 0.5 ml of serum free medium is added and cells are incubated at 37° C. cell culture incubator for 10 minutes. In the case of the treatment with glutamate or other neurotoxins to induce apoptosis, the identified JNK or MLK inhibitor is added to the serum-free medium and incubation continued for another 5 minutes. Then glutamate or neurotoxin are added to the medium. If the JNK or MLK inhibitor is effective, the amount of apoptotic cells will be significantly reduced or totally inhibited, as compared with the appropriate control. Such a result indicates that these inhibitors are effective for the prevention of neuronal death in various neurological disorders. In the case of expression of mutated huntingtin or APP-C-100 (vector which expresses the c-terminal 100 amino acids of APP) to induce apoptosis, the JNK or MLK inhibitor is added during or 2–6 hours after transfection. In a particular embodiment, the $IC_{50}$ of the JNK or MLK inhibitors in suppression of neuronal apoptosis can be also assessed by this 96-well based assay. In this case, different concentrations of JNK or MLK inhibitor are added to the medium prior to the treatment with glutamate or other neurotoxins or during transfection of the mutated huntingtin or APP to establish a pharmacological profile for each inhibitor. The $IC_{50}$ of each inhibitor is a very important value for designing further study of the effectiveness in different animal models and for directing clinical trials of these inhibitors.

The present invention also pertains to methods for the prevention or treatment of neurological conditions, either through prophylatic administration prior to the occurrence of an event known to cause a neurological condition or therapeutic administration immediately following the event and periodically thereafter. Such prophylatic and therapeutic treatments are intended to prevent neuronal cell death or reduce the degree of cell death. Given the involvement of JNK and MLK in the cascade leading to neuronal cell death, these two kinases present targets for a therapeutic regime. According to the method, a mammal, including human, is administered an effective therapeutic amount of an agent that targets JNK- and/or MLK-associated activity. A therapeutic amount for a given agent is that amount administered to achieve the desired result, for example, the inhibition of kinase activity in either JNK or MLK or both, or attenuation, amelioration of or improvement in the symptoms associated with the neurological condition.

In one embodiment, the JNK-associated activity that is targeted is JNK's kinase activity. By inhibiting JNK's activity with an agent, neuronal cell death can be avoided. The JNK activity to be targeted includes JNK1, JNK2 and JNK3.

In another embodiment, the enzyme activity targeted is MLK. If MLK is not inhibited, then it will directly bind to and phosphorylate SEK1 resulting in its activation which in turn will stimulate JNK, thereby causing neuronal cell death. By inhibiting MLK activity, including MLK1, MLK2 and MLK3, the SEK1 phosphorylation and concomitant stimulation can be eliminated, thereby saving neuronal cells from apoptosis. This therapeutic approach can be used to prevent and/or treat neurological conditions, as described above. The inhibitory agents identified using the methods described herein are particularly useful for suppressing glutamate receptor-induced activation of JNK, glutamate-mediated toxicity and apoptosis caused by excitotoxicity.

Compounds identified using the methods described herein are designed to selectively inhibit the neuronal isoform of kinase which is involved in neuronal loss in neurodegenerative diseases. These kinase inhibitors will selectively decrease a specific kinase activity in neurons and protect neurons from a variety of oxidative stimuli thereby allowing a broad range of clinical applications. Because the neuronal isoform of kinase is selectively attenuated, side effects in peripheral tissues may be neglectable and because other isoforms of the kinase are present in neurons and will provide complementary function for the inhibited isoforms of the kinase, side effects in the central nervous system may also be minimal. A specific inhibitor of MLK2 or JNK3 should be an effective, low toxic neuroprotective drug for the treatment of a wide range of neurodegenerative disorders. In particular, two different kinases on the same signaling pathway can be targeted. These different kinase inhibitors with similar clinical effects will allow to develop a clinical protocol to avoid drug tolerance and provide a life-long treatment.

Inhibitory agents of JNK, MLK or both, identified according to the methods of this invention, can be administered subcutaneously, intravenously, parenterally, intraperitoneally, intradermally, intramuscularly, topically, enteral (for example, orally), rectally, nasally, buccally, vaginally, by inhalation spray, by drug pump or via an implanted reservoir in dosage formulations containing conventional non-toxic, physiologically (or pharmaceutically) acceptable carriers or vehicles.

In a specific embodiment, it may be desirable to administer the agents of the invention locally to a localized area in need of treatment, this may be achieved by, for example, and not by way of limitation, local infusion during surgery, topical application, transdermal patches, by injection, by means of a catheter, by means of a suppository, or by means of an implant, said implant being of a porous, non-porous, or gelatinous material, including membranes, such as sialastic membranes or fibers.

In a specific embodiment when it is desirable to direct the drug to the central nervous system, techniques which can opportunistically open the blood brain barrier for a time adequate to deliver the drug there through can be used. For example, a composition of 5% mannitose and water can be used. The present invention also provides pharmaceutical compositions. Such compositions comprise a therapeutically (or prophylactically) effective amount of the agent, and a physiologically acceptable carrier or excipient. Such a carrier includes, but is not limited to, saline, buffered saline, dextrose, water, glycerol, ethanol, and combinations thereof. The carrier and composition can be sterile. The formulation should suit the mode of administration.

Suitable pharmaceutically acceptable carriers include but are not limited to water, salt solutions (for example, NaCl), alcohols, gum arabic, vegetable oils, benzyl alcohols, polyethylene glycols, gelatin, carbohydrates such as lactose, amylose or starch, magnesium stearate, talc, silicic acid, viscous paraffin, perftime oil, fatty acid esters, hydroxymethylcellulose, polyvinyl pyrolidone, etc. The pharmaceutical preparations can be sterilized and if desired, mixed with auxiliary agents, for example, lubricants, preservatives, stabilizers, wetting agents, emulsifiers, salts for influencing osmotic pressure, buffers, coloring, flavoring and/or aromatic substances and the like which do not deleteriously react with the active compounds.

The compositions, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium sterate, polyvinyl pyrollidone, sodium saccharine, cellulose, magnesium carbonate, etc.

The compositions can be formulated in accordance with the routine procedure as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed prior to administration.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, enemas, lotions, sols, liniments, salves, aerosols, etc., which are, if desired, sterilized or mixed with auxiliary agents, for example, preservatives, stabilizers, wetting agents, buffers or salts for influencing osmotic pressure, etc. The drug may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

The amount of agents which will be effective in the treatment of a particular disorder or condition will depend on the nature of the disorder or condition, and can be determined by standard clinical techniques. In addition, in vitro or in vivo assays may optionally be employed to heip identify optimal dosage ranges. The precise dose to be employed in the formulation will also depend on the route of administration, and the seriousness of the disease or disorder, and should be decided according to the judgment of the practitioner and each patient's circumstances.

The invention will now be further and specifically described by the following examples which are not intended to be limiting in any way. All publications cited herein are incorporated by reference in their entirety.

EXAMPLES

Example 1

Developing a Model for Neurodegeneration Based on Huntingtin Expression

To develop a cell-based system in which apoptosis can be induced, polyglutamine-expanded huntingtin was introduced into cell lines.

To assess whether polyglutamine-expanded huntingtin causes toxicity, full-length huntingtin expression constructs containing 16, 48 or 89 CAG repeats were generated by assembly of a combination of RT-PCR products from normal and human HD lymphoblast and plasmid cDNA clones IT16L and IT15B, which are described in HD Collaborative Research Group, Cell 72:971–983 (1993).

To construct the huntingtin expression vector with 16, 48, or 89 CAG repeats, the first third of the full-length construct was derived by ligation of IT16LL (bp 932–3018) with three different PCR products (bp 2401–3270, bp 637–1429 and 187–858). A 3027 bp cDNA fragment was removed from the resulting construct and ligated to corresponding sites in the cDNA clones IT15B (bp3024–10366). The CAG repeat size in the full length huntingtin construct pFL16HD was 16. PCR products were generated from the genomic DNA of an adult patient with 48 CAG repeats and a juvenile onset case with 89 CAG repeats. These PCR products replaced the corresponding region in pFL16HD to generate the pFL48HD and pFL89HD with 48 and 89 CAG repeats, respectively. Colony hybridization and PCR were used to identify the 48 and 89 CAG huntingtin clones and the positive clones were verified by DNA sequence analysis.

The resulting constructs pFL16HD, pFL48HD or pFL89HD were transiently transfected into 293 embryonic kidney cells, and expression of huntingtin was analyzed by immunoblotting using the anti-huntingtin monoclonal antibody 4C8. Trottier, Y., et al., Nature Genet., 10:104–110 (1995).

For transient expression of normal and polyglutamine-expanded huntingtin, 50% to 60% confluent HN33 or 293 cells were washed once with serum free medium prior to transfection. Transfection was performed by using lipofectin (Boehringer Mannheim) according to manufacturer instructions and fetal bovine serum was added to the medium 12 hours after transfection to a final concentration of 1%. Sixty µg of plasmid with 10 µl of lipofectin /60 mm plate was used in all transfection experiments. After 72 hours, the transfection medium was removed and replaced by fresh medium with 1% fetal bovine serum. For immunoprecipitation and Western blotting, 293 cells were harvested 48–72 hours after transfection and lysed in 1% NP-40 lysate buffer. For the immunoprecipitation experiment, cell lysates were incubated with an affinity-purified anti-N-terminus huntingtin polyclonal antibody 437 for 4–6 hours. Liu, Y. F., et al., J. Biol. Chem., 272:8121–8124 (1997). Cell lysates or precipitated proteins were resolved on SDS-PAGE, transferred and immunoblotted with an anti-huntingtin monoclonal antibody 4C8. All three huntingtin constructs constitutively expressed the huntingtin protein. Transfection of pcDNA1 (vector) or normal huntingtin with 16 CAG repeats (pFL16HD) did not lead to toxicity in HN33 cells. In addition, DNA fragmentation was not detectable using Tdt-mediated dUTP-biotin nick end labeling (TUNEL) assay. However, cell proliferation was slightly suppressed.

The TUNEL assay was performed by using a TUNEL assay kit (Boehringer Mannheim). HN33 cells were plated on a slide culture chamber. Transient transfection as conducted as described above. Transfection medium was removed at specified times post-transfection. The cells were washed once with serum free medium, fixed with 4% paraformaldehyde and then perneabilized with 01% of Triton X-100. The TUNEL assay was performed as described in the manufacturer's instructions provided with the kit.

Expression of mutated huntingtin with 48 or 89 CAG repeats (pFL48HD or pFL89HD) induced cell toxicity in HN33 cells. Apoptosis was initially observed between 20 and 24 hours after transfection by TUNEL staining. At 48 hours, about 75% of transfected cells were apoptotic.

A time-course of HN33 cell survival after transfection with pcDNA1, pFL16HD, pFL48HD or pFL89HD was performed forty eight hours after transfection, HN33 cells were fixed and stained with TUNEL. Living and apoptotic cells were counted in the high power field. The number of living cells in pcDNA1 transfectants is designated as 100%. FIG. 1 indicates that, cell toxicity induced by transfection of pFL89HD was slightly more severe than that mediated by pFL48HD, while transfection of pcDNA1 or pFL16HD did not produce measurable neuronal toxicity. Each data point in FIG. 1 is an average of four independent experiments.

Figure 2:
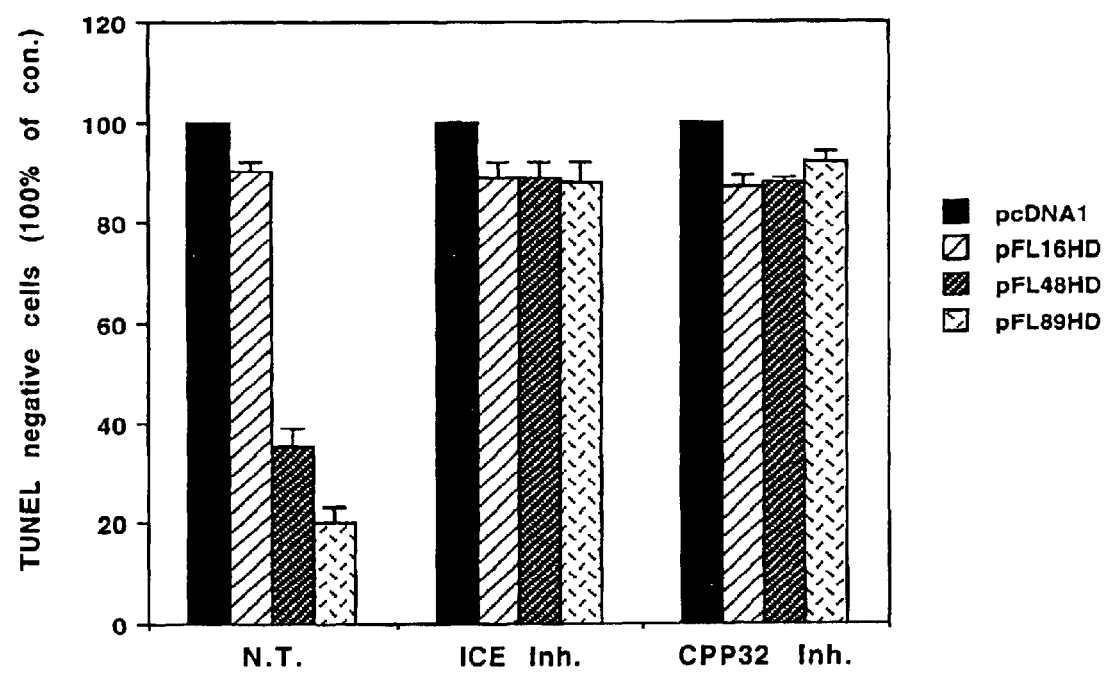
FIG. 2 is a graph illustrating apoptotic cell death induced by expression of mutated huntingtin with 48 or 89 polyglutamine repeats was completely blocked by added the ICE or CPP32 inhibitor in the medium indicating HN33 cells are undergoing apoptotic cell death.

To further confirm that the polyglutamine-expanded huntingtin-induced cell death described above was apoptotic, the interleukin 1 β converting enzyme (ICE) inhibitor zVAD-frm (Sarin et al., J. Exp. Med 184:2445–2449 (1996)) or CPP32 inhibitor zDEVD-frm (Rodgriguez et al, J. Exp. Med. 184:2067–2072 (1996)) was added to the medium during transfection to a inhibitor concentration of 10 µg/mL. Both inhibitors were obtained from Enzyme System Products, Inc. It was shown that ICE and CPP32participated in apoptosis and that inhibitors zVAD-frm and zDEVD-frm blocked mutated huntingtin-mediated apoptotic cell death at 48 hours post-transfection (FIG. 2). ICE cleaves inactive CPP32 participated in apoptosis and that inhibitors zVAD-frm and zDEVD-frm blocked mutated huntington-mediated apoptotic cell death at 48 hours post-transfection (FIG. 2). (Vaux et al., Proc. Natl. Acad. Sci. USA, 93:2239–2244(1996)). It was known that ICE cleaves inactive CPP32 precursor thereby activating the enzyme. This result therefore suggests that expression of polyglutamine-expanded hungtingtin stimulates ICE, which in turn activates CPP32 to induce apoptotic cell death.

Example 2

Role of JNK in Neuronal Apoplosis

Whether expression of polyglutamine-expanded huntingtin induces activation of JNK was investigated. GST c-Jun (1–89 aa) was utilized as a substrate to measure JNK activity in cell lysates from HN33 cells transfected with pcDNA1 (control), pFL16HD, pFL48HD or pFL89HD.

HN33 cells were lysed with 1% Triton buffer 16 hours after transfection. Cell lysates were incubated with glutatione-S-transferase (GST)-c-jun (1–89) fusion protein immobilized on glutatione sepharose beads to isolate JNK. These beads were resuspended in 30 µL kinase buffer. The kinase reaction was performed at 30° C. for 30 minutes and then stopped by adding SDS sample buffer to the reaction. The reaction was analyzed by Western blotting using a phospho (ser63)-specific c-jun antibody (New England BioLabs).

Figure 3:
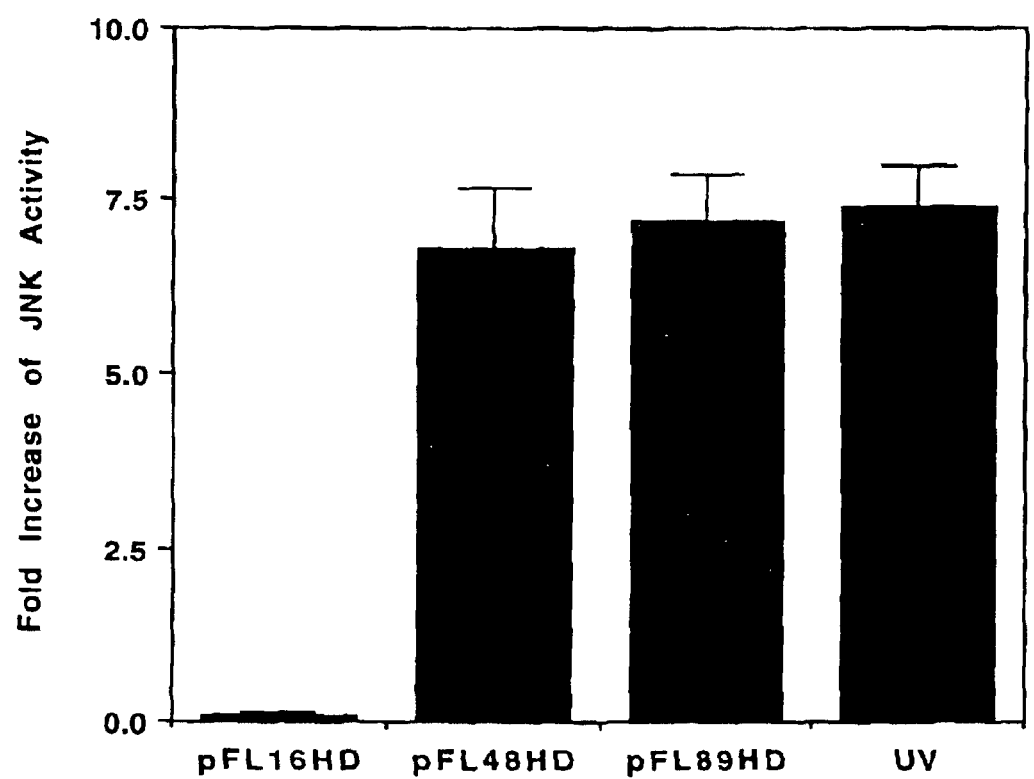
FIG. 3 is a graph illustrating the fold of increased JNK activity in HN33 cells upon expression of mutated huntingtin with 48 or 89 polyglutamine repeats.

A low level of JNK activation was observed in control cells. Transfection of a plasmid encoding normal huntingtin with 16 CAG repeats did not further increase the amount of serine phosphorylated GST c-Jun and thus did not stimulate JNK activity. Expression of mutated huntingtin with 48 or 89 CAG repeats, however, significantly increased the levels of JNK activity. Serine phosphorylated GST c-Jun was increased 7 to 8-fold, similar to the level induced by 30 minutes of ultraviolet light irradiation. These results indicated that polyglutamine repeat expansion in huntingtin activated JNK in HN33 cells (FIG. 3).

Whether activation of JNK is responsible for polyglutamine-expanded huntingtininduced apoptotic cell death in HN33 cells was next examined. It was known that JNK is specifically activated by SEK1, which is a dual-specificity kinase that phosphorylates both tyrosine and threonine residues of JNK, thereby activiting it Sanchez el al., Nature, 380:75–79 (1994)). A dominant negative mutant of SEK1 (K54R), known to specifically block JNK activation (Lin et al., Science, 268:286–290 (1995); Yan et al., Nature, 372:798–800 (1994)) was used.

Figure 4:
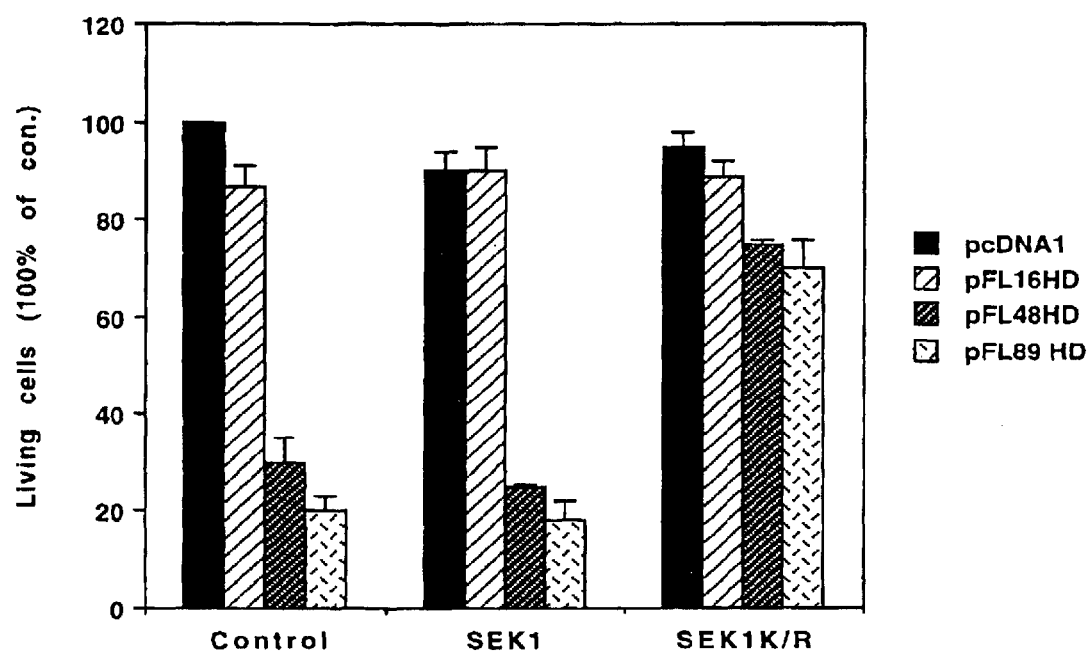
FIG. 4 is a graph illustrating apoptotic cell death of HN33 cells induced by mutated huntingtin with either 48 or 89 polyglutamine repeats was inhibited by co-expression of dominant negative mutant form of SEK1 but not wild-type SEK1.

HN33 cells were transiently transfected with various expression plasmids, including the SEK1 and SEK1 (K54R) expression vectors described in Lin, A., et al., Science, 268:286–290 (1995). Forty-eight hours after transfection, the cells were fixed and subjected to the TUNEL assay as described above. The number of living cells transfected with pcDNA1 was designated at 100%. The data is summarized in FIG. 4. Each data point represents an average of three independent experiments.

Transient expression of wild-type or dominant negative SEK1 alone had little effect on the proliferation and survival of HN33 cells. Co-expression of pcDNA1 with pEBG (SEK1 expression vector backbone control plasmid) also did not lead to cell toxicity. However, co-transfection of wild-type SEK1 vector with pFL48HD or pFL89HD did not affect neuronal toxicity induced by mutated huntingtin. Co-expression of dominant negative mutant SEK1 (K54R) significantly prevented apoptotic cell death induced by mutated huntingtin. At 48 hours after transfection, about 25% to 30% of cells had undergone apoptosis, compared to about 75% of cells containing pFL48HD or pFL89HD alone.

The foregoing data showed that a specific inhibitor of JNK, SEK1 (K54R), can inhibit polyglutamine-expanded huntingtin-induced apoptosis and may be a useful drug for treating a neurological condition. Thus it was possible to test a compound's potential as a drug by contacting the compound with a JNK inside a cell.

Figure 5:
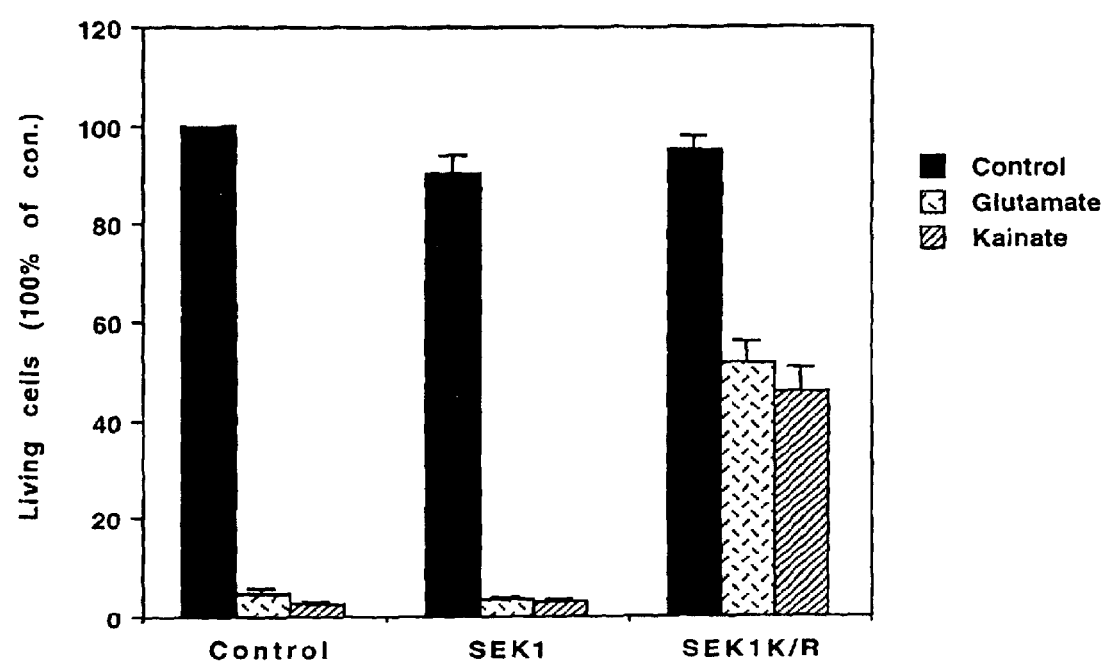
FIG. 5 is a graph illustrating apoptotic cell death of HN33 cells induced by the treatment of glutamate (250 $\mu$M) or kainic acid (kainate, 200 $\mu$M) was significantly attenuated by expression of dominant negative mutant form of SEK1 (K54R) but not wild-type SEK1, indicating that glutamate or kainate induced the activation of the SEK1-JNK pathway to mediate neuronal apoptosis.

To determine whether the SEK1-JNK signal transduction pathway is involved in neuronal cell death induced by excitotoxicity induced by glutamate or kainate receptors, HN33 cells were transfected with pEBG (SEK1 expression vector backbone control plasmid), wild-type SEK1 expression vector, or dominant negative mutant SEK1(K54R) expression vector. Forty-eight hours after transfection, the media covering the cells was replaced with fresh serum-free media supplemented without (control) or with 250 $\mu$M glutamate or 200 $\mu$M kainic acid (kainate). Cells were incubated in 37° C. for six hours. Then cells were fixed and stained with TUNEL. TUNEL negative cells (living cells) were counted. The results in FIG. 5 show that SEK1 (K54R) blocks apoptosis induced by glutamate or kainate receptor activation. Each data point represents the average of three independent experiments.

Figure 6:
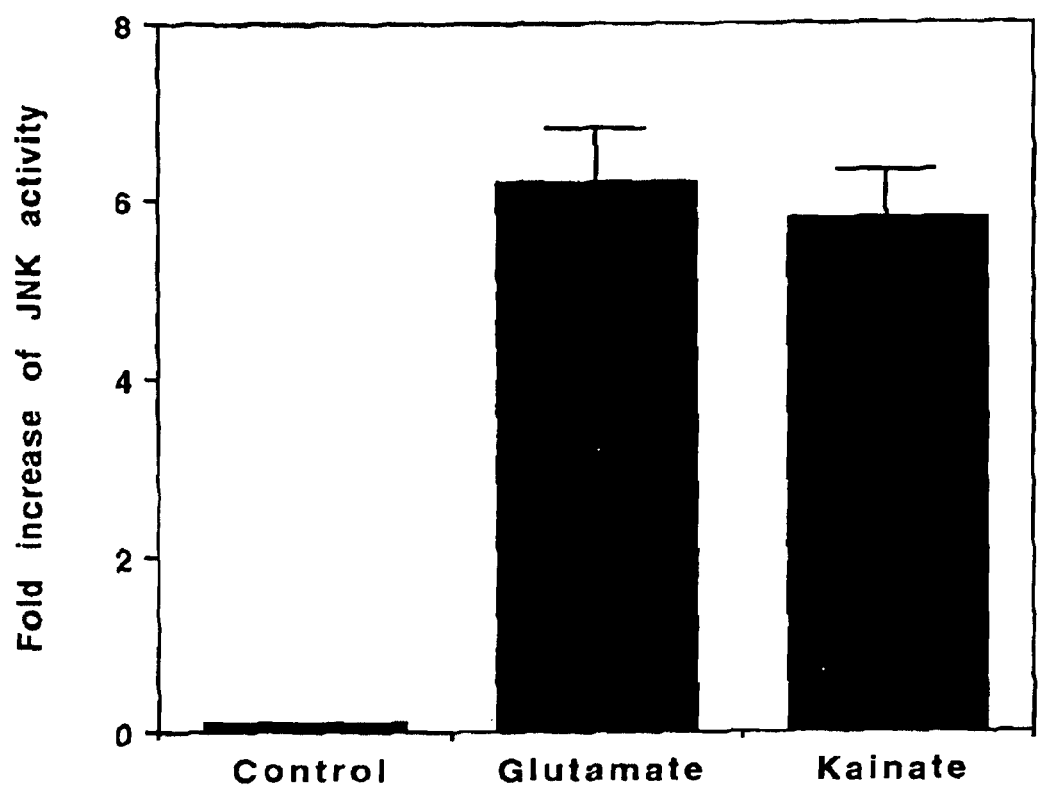
FIG. 6 is a graph illustrating the fold of increased JNK activity in HN33 cells upon stimulation of glutamate or kainate receptor indicating that glutamate or kainate receptor activation also stimulated the JNK activity like expression of mutated huntingtin.

To determine further the role of JNK in glutamate-induced neuronal apoptosis, HN33 cells were treated with glutamate (250 $\mu$M) or kainic acid (200 $\mu$M) at room temperature for 15 minutes and then lysed in 1% Triton X-100 buffer. Cell lysates were incubated with GST-c-Jun (1–89) fusion protein immobilized on glutathione sepharose beads to isolate JNK. These beads were resuspended in 30 $\mu$l kinase buffer and the kinase reaction was performed at 30° C. for 30 minutes and 10 $\mu$l SDS sample buffer was added to stop the reaction. The samples were resolved by electrophoresis and transferred to a PVDF membrane (Millipore) and the JNK activity was analyzed by Western blotting using a phospho (Ser63)-specific c-Jun antibody (New England Biolabs). The results in FIG. 6 show that glutamate or kainate receptor activation induced elevation of the JNK activity. Each data point represents an average of three independent experiments.

Figure 7:
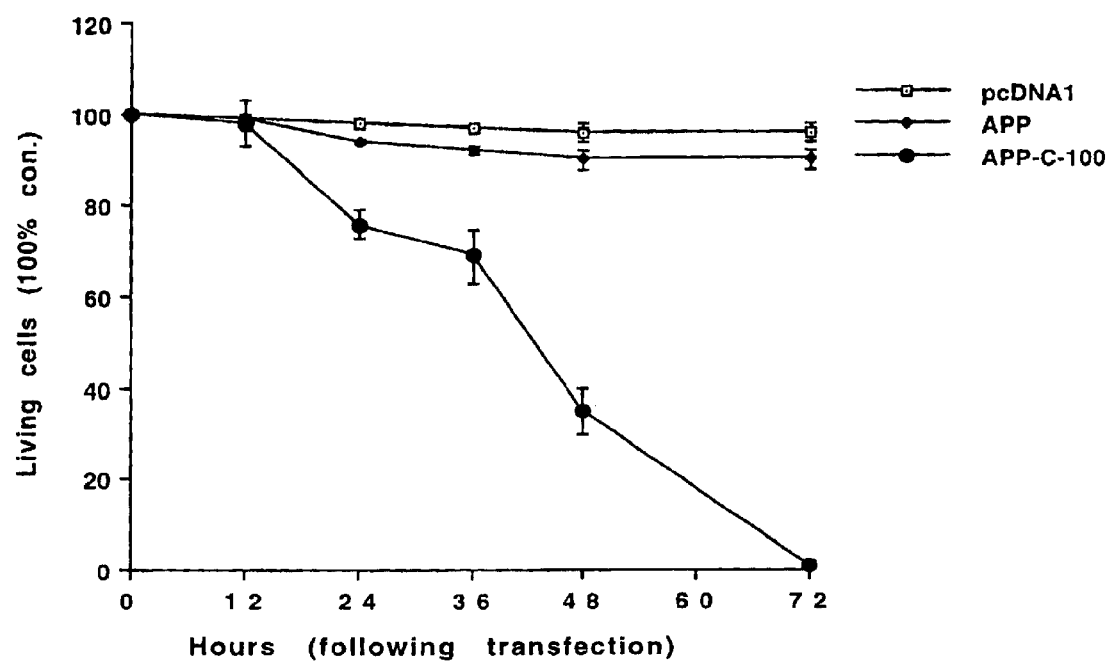
FIG. 7 is a graph illustrating a time course of cell death upon following transfection of pcDNA1 (control) APP or APP deletion mutant APP-C-100, pcDNA1 (open box), wild-type APP (solid diamond), APP-C-100 (solid circles).

To determine the role of activation of the SEK1-JNK signal transduction pathway in Alzheimer's diseases, a cDNA fragment encoding the full-length (Kang, J., et al., Nature, 325:733–736 (1987)) or the last C-terminal 100 amino acid of amyloid precursor protein (APP) was inserted into pcDNA1 and the resulting plasmid was designated as APP-C-100. HN33 cells (60% of confluence) was transfected with pcDNA1 (control), wild-type APP, APP-C-100 by using lipofectin (Boehringer Mannheim) according to manufacture instruction. Thirty $\mu$l of lipofectin/50 mm plate was used in all transfection experiments. Twelve to seventy-two hours after transfection, HN33 cells were fixed with 4% paraformaldehyde and permeabilized with 0.1% of Triton X-100. The TUNEL staining was performed by using a TUNEL staining kit (Boehringer Mannheim) as described in manufacture instructions provided with the kit. TUNEL negative cells were counted under light microscope. The results in FIG. 7 show that expression of APP-C-100 induced rapid neuronal apoptosis. Cell death was initially observed between twenty to twenty-four hours after transfection and at seventy-two hours, all cells were apoptotic, while expression of pcDNA1 (control) or wild-type APP did not induce neuronal cell death.

Figure 8:
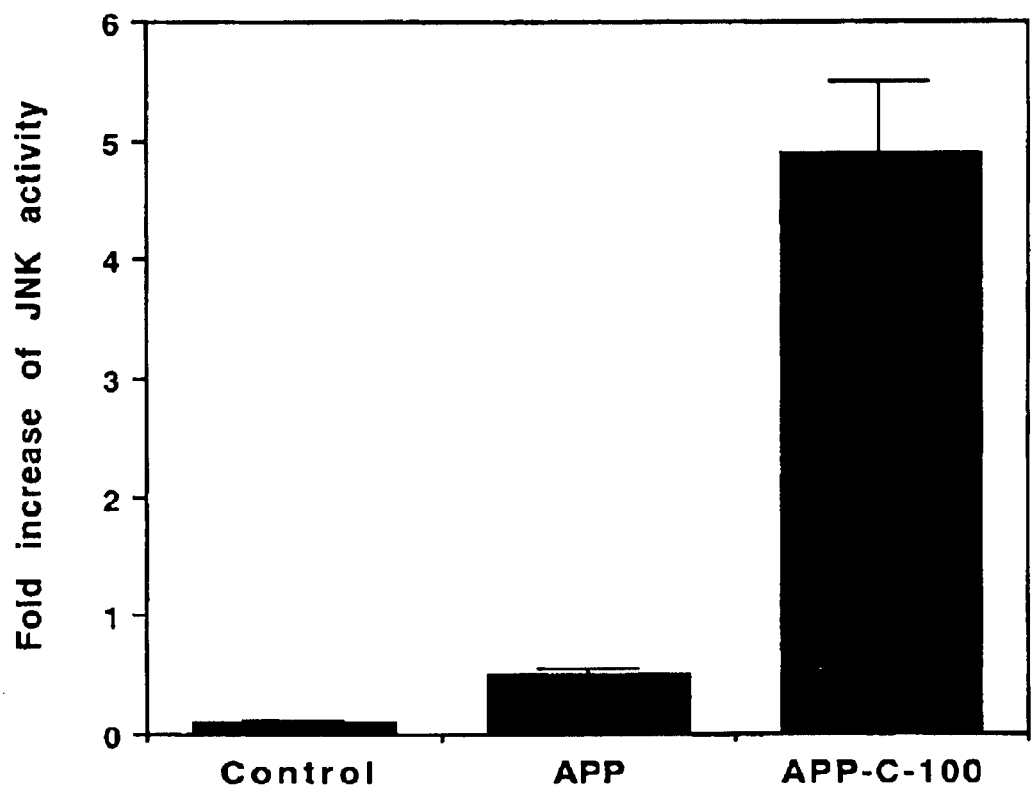
FIG. 8 is a graph illustrating the fold of increased JNK activity in HN33 cells following transfection of pcDNAI (control) APP or APP deletion mutant APP-C-100, indicating that expression of APP-C-100 stimulated the JNK activity.

To determine the role of the JNK activity in neuronal cell death induced by APP-C-100, HN33 cells were transiently transfected with pcDNAI, wild-type APP or APP-C-100 using lipofectin as described above. After eighteen hours, cells were lysed in 1% Triton C-100 buffer. Cell lysates were incubated with GST-c-Jun (1–89) fusion protein immobilized on glutathione sepharose beads to isolate JNK. These beads were resuspended in 30 $\mu$l kinase buffer and the kinase reaction was performed at 30° C. for 30 minutes and 10 $\mu$l SDS sample buffer was added to stop the reaction. The JNK activity was analyzed by Western blotting using a phospho (Ser63)-specific c-Jun antibody (New England BioLabs). The results in FIG. 8 show that expression of APP-C-100 but not wild-type APP stimulated the JNK activity in HN33 cells.

Figure 9:
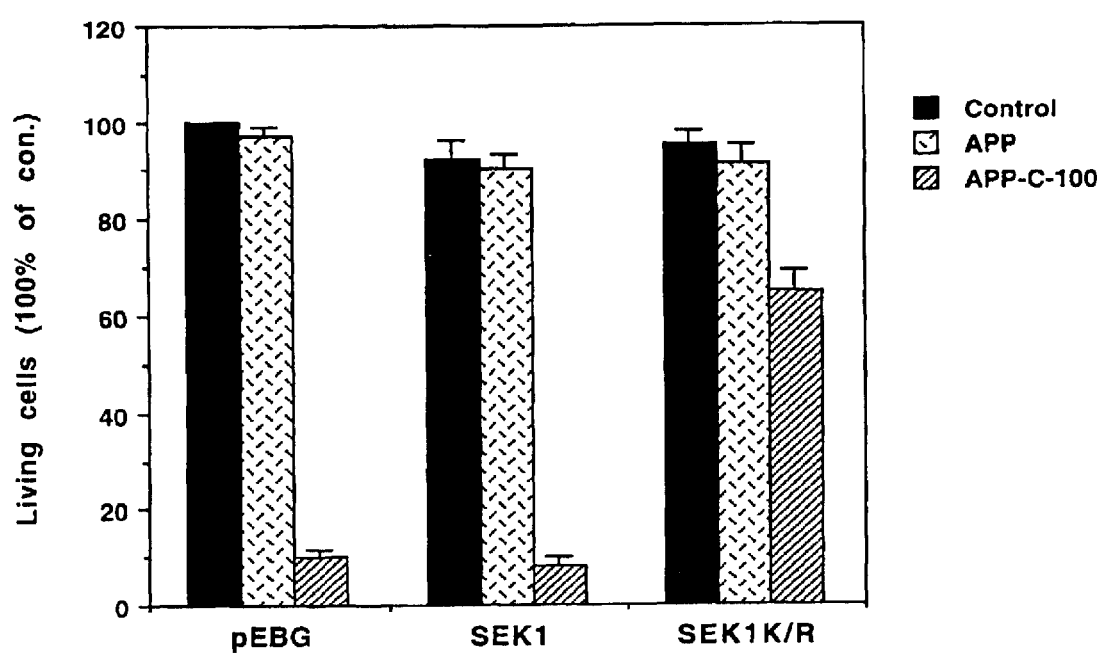
FIG. 9 is a graph illustrating apoptotic cell death of HN33 cells induced by expression of APP-C-100 was significantly attenuated by co-expression of dominant negative mutant form of SEKI (K54R) but not wild-type SEK1, indicating that amyloid precursor protein induced the activation of the SEK1-JNK pathway to mediate neuronal apoptosis.

To further determine the role of activation of the JNK activation in Alzheimer's diseases, HN33 cells were transfected with pcDNA 1, wild-type APP expression vector, or mutant SEK1 expression vector using lipofectin (Boehringer Mannheim) according to manufacture instruction. Forty-eight hours after transfection, cells were fixed and stained with TUNEL. TUNEL negative cells (living cells) were counted. The results in FIG. 9 show that SEK1 (K54R) blocks apoptosis induced by expression of APP-C-100.

Taken together, these results indicate the elevation of the JNK activity is a common cause of neuronal cell death, regardless of the cause. Since excitotoxicity is a final common pathway for neuronal loss in neurodegenerative disease as well as in acute insults, inhibition of the JNK activity will prevent neuronal death in these neurological conditions.

Example 3

Role of MLK in Neuronal Apoptosis

A kinase dead version of MLK2 was generated by introduction of A–G point mutation at position 651 (codon AGG to GAG) by overlapping extension using polymerase chain reaction with mutated oligonucleotides, to result in amino acid substitution of K to E in the ATP binding loop of the MLK2 kinase domain. Such a point mutation leads to total loss of kinase activity of MLK2 and a kinase dead version of MLK2 will act as a dominant mutant and inhibit MLK2 activation-mediated actions. Tibbles, L. A., et al., *EMBO. J.*, 15:7026–7036 (1996). The CDNA fragment of wild-type or kinase dead MLK2 was inserted into pRK5CMV with a C-terminal myc tag. Nagata, K., et al., *EMBO. J.*, 17:149–158 (1998).

Figure 10:
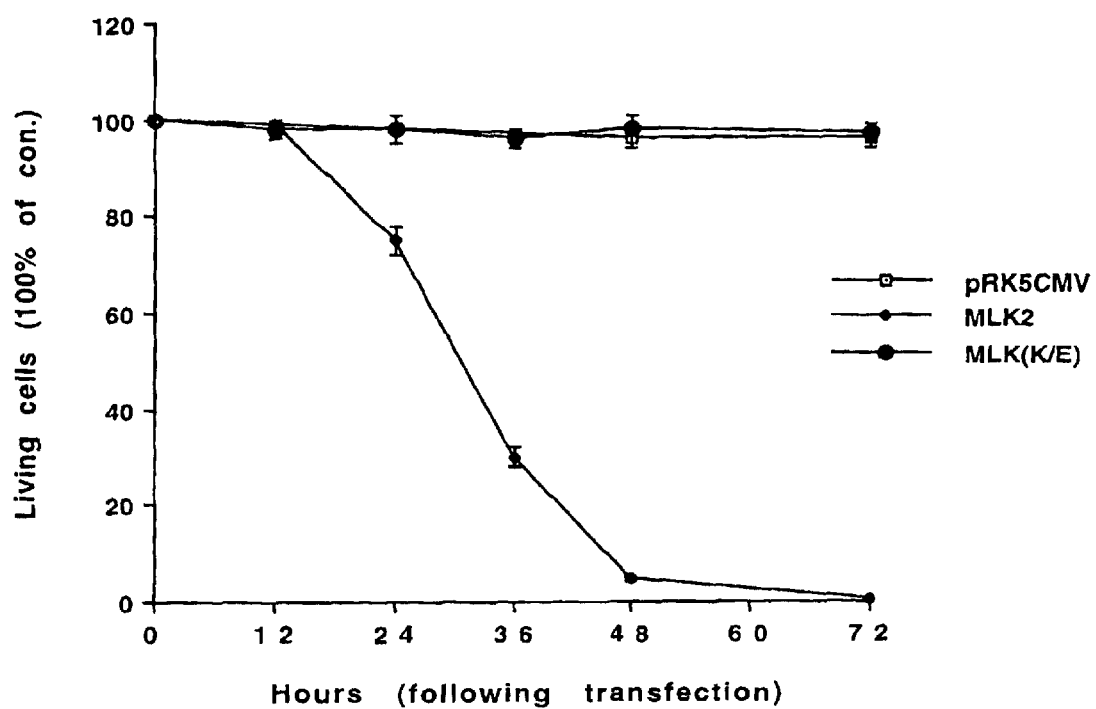
FIG. 10 is a graph illustrating a time course of cell death following transfection of pRK5CMV (control), wild-type MLK2 or kinase dead version of MLK2, pRK5CMV (open box), wild-type MLK2 (solid diamond), kinase dead MLK2 (solid circles).

To examine whether expression of MLK2 induces neuronal cell death, HN33 cells were transfected with pRK5CMV, wild-type or kinase dead MLK2 expression vector using lipofectin (Boehringer Mannheim) according to manufacture instruction. Forty-eight hours after transfection, cells were fixed and stained with TUNEL, as described above. TUNEL negative cells (living cells) were counted. The results in FIG. 10 show that expression of MLK2 induced apoptosis in HN33 cells while expression of the kinase dead version of MLK2 did not generate any cell toxicity.

Figure 11:
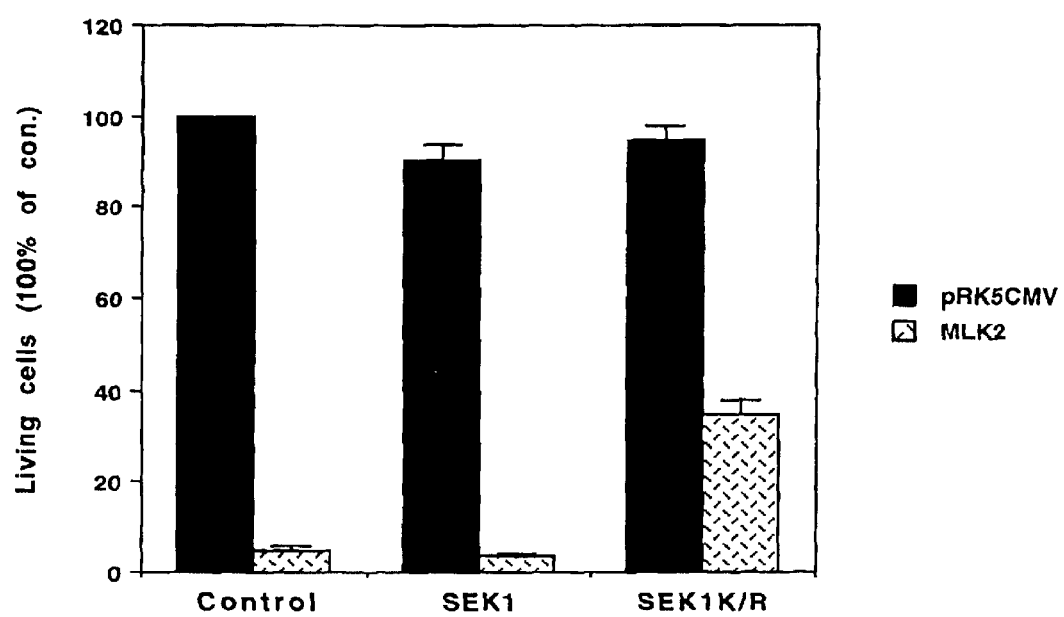
FIG. 11 is a graph illustrating apoptotic cell death of HN33 cells induced by expression of MLK2 was significantly attenuated by co-expression of dominant negative mutant form of SEK1 (K54R) but not wild-type SEK1, indicating that MLK2 induced the activation of the SEK1-JNK pathway to mediate neuronal apoptosis.

To determine whether the role of the SEK1-JNK signal transduction pathway in neuronal cell death induced by expression of MLK2, HN33 cells were co-transfected with pEBG+pRK5CMV (control), wild-type SEK1 expression vector+wild-type MLK2 expression vector, or dominant negative mutant SEK1 (K54R) expression vector +wild-type MLK2 expression vector. Forty-eight hours after transfection, cells were fixed and stained with TUNEL. TUNEL negative cells (living cells) were counted. The results in FIG. 11 show that SEK1 (K54R) attenuated apoptosis induced by MLK expression.

Figure 12:
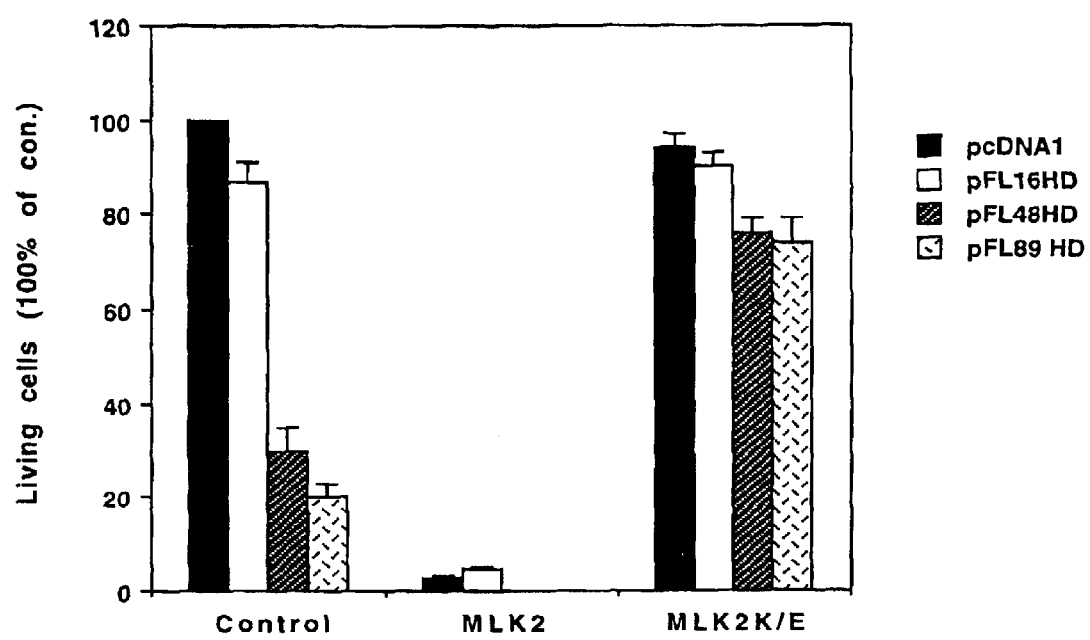
FIG. 12 is a graph illustrating apoptotic cell death of HN33 cells induced by expression mutated huntingtin with 48 or 89 CAG repeats was blocked by co-expression of kinase dead MLK2, indicating that the MLK2-associated activity mediated neuronal cell death in Huntington's diseases.

To determine the role of MLK2 in neuronal loss in Huntington's disease, HN33 cells were co-tranfected with pEBG+pRK5CMV (control), normal huntingtin expression vector with 48 or 89 CAG repeats+kinase dead MLK2 epression vector. Forty-eight hours after transfection, cells were fixed and stained with TUNEL. TUNEL negative cells (living cells) were counted. The results in FIG. 12 show that coexpression of kinase dead MLK2 blocked neuronal apoptosis induced mutated huntingtin and demonstrated that the MLK-associated activity was involved in neuronal loss in Huntingtin's dieases.

The potential association of huntingtin with MLK2 was examined in 293 cells transfected with MLK2, normal huntingtin, or polyglutamine-expanded huntingtin in 293 cells at 48 hours after transfection. Expression of normal or mutated huntingtin failed to activate JNKs. Since 293 cells are rich in huntingtin (Liu, Y.F., et al., *J. Biol. Chem.*, 272:8121–8124 (1997)), the interaction of MLK2 with normal huntingtin in 293 cells was examined. C-Myc tagged MLK2 was transiently expressed in 293 cells, and MLK2 was precipitated with anti-c-myc tag 9E 10 antibody (Santa Crutz).

C-myc-tagged MLK2 was transiently expressed in 293 cells, as described above, 48–72 hours after transfection, 293 cells were harvested and lysed in 1% NP-40 lysa buffer. Cell lysates were incubated with an anti-N-terminus huntingtin antibody 437 or 9E10 for 4–6 hours. The precipitated proteins were resolved on SDS-PAGE, transferred, and immunoblotted with an anti-huntingtin monoclonal antibody 4C8, or anti-c-myc antibody 9E10.

In cell lysates from 293 cells transfected without or with pRK5CMV control vector described above, 9E10 failed to co-precipitate huntingtin. However, when the 293 cells were transfected with c-myc tagged MLK2, huntingtin was easily detected in both 9E10 and 4C8 (anti-huntingtin) immunoprecipitates. Thus, MLK2 is associated with huntingtin.

Conversely, whether an anti-huntingtin antibody precipiated MLK2 was determined. Cell lysates from 293 cells with or without transfection of a MLK2expression vector were incubated with 437, an anti-huntingtin antibody, or 9E10. MLK2 was detectable in both 9E10 and 437 immunoprecipitates of 293 cell lysates transfected with MLK2. In non-tranfected 293 cells, MLK2 was not found in either 9E10 or 437 immunoprecipitates. These results demonstrate that huntingtin is associated with MLK2 in vivo.

Next, we tried to examine the novel association of MLK2 with mutated huntingtin containing 48 CAG repeats in 293 cells. Expression of MLK2 or mutated huntingtin alone did not generate any cell toxic effect. Co-expression of MLK2 with normal huntingtin containing 16 CAG repeats also did not produce any cell toxicity while co-expression of mutated huntingtin with induced rapid cell death.

Figure 13:
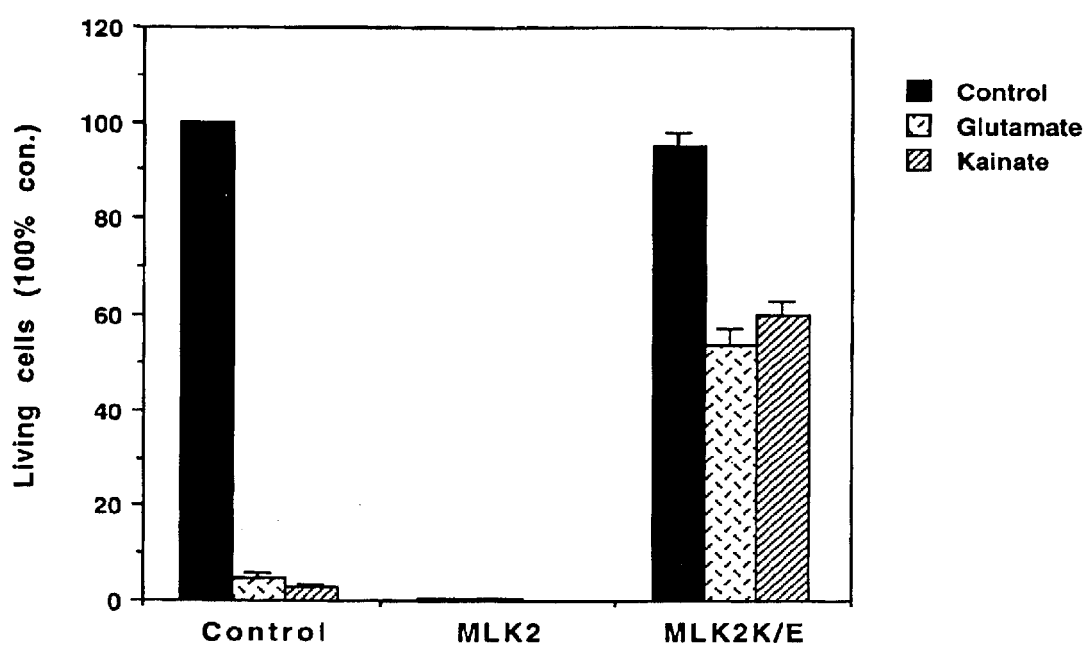
FIG. 13 is a graph illustrating apoptotic cell death of HN33 cells induced by the treatment of glutamate (250 $\mu$M) or kainic acid (kainate 200 $\mu$M) was blocked by expression of kinase dead MLK2 indicating that the MLK2-associated activity mediated neuronal cell death in neuronal excitotoxicity induced by glutamate or kainate receptor activation.

To determine whether the role of MLK2 in neuronal cell death induced by glutamate or kainate receptor activation, HN33 cells were transfected with pRK5CMV (control) or kinase dead MLK2 expression vector. Forty-eight hours after transfection, the media covering the cells was replaced with fresh serun-free media supplemented without (control) or with 250 $\mu$M glutamate or 200 $\mu$M kainate. Cells were incubated in 37° C. for six hours, fixed, and then stained with TUNEL. TUNEL negative cells (living cells) were counted. The results in FIG. 13 show that kinase dead MLK2 blocks apoptosis induced by glutamate or kainate receptor activation in HN33 cells.

Figure 14:
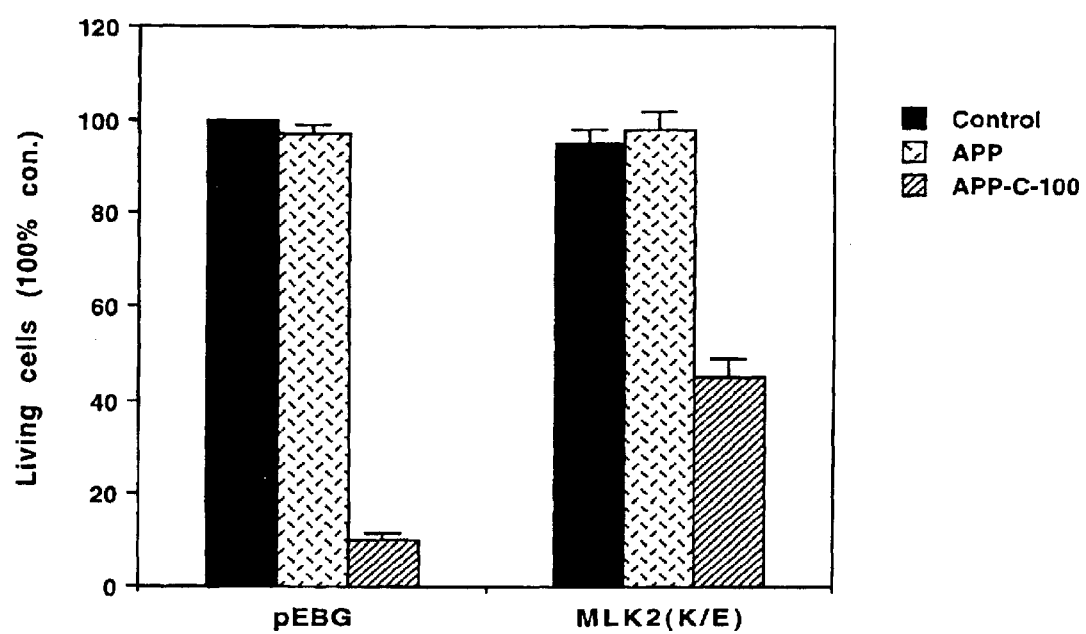
FIG. 14 is a graph illustrating apoptotic cell death of HN33 cells induced by expression of deletion APP mutant APP-C-100 was blocked by co-expression of kinase dead MLK2, indicating that the MLK2-associated activity mediated neuronal cell death in Alzheimer's diseases.

To determine further the role of activation of the MLK activation in Alzheimer's diseases, HN33 cells were co-transfected with pcDNA1, wild-type expression vector, with kinase dead MLK2 expression vector. Forty-eight hours after transfection, cells were fixed and stained with TUNEL. TUNEL negative cells (living cells) were counted. The results in FIG. 14 show that kinase dead MLK2 blocks apoptosis induced by expression of APP-C-100.

Taken together, these results shown that the MLK-associated activity mediated neuronal degeneration in Huntington's disease, Alzheimer's disease and excitotoxicity induced by glutamate or kainate receptor activation. Since excitotoxicity is a final common pathway for neuronal loss in neurodegenerative disease as well as in acute insults, inhibition of the MLK2 activity will prevent neuronal death in these neurological conditions.

Example 4

Preparation and purification of GST Fusion proteins

Glutathione-S-transferase (GST)) c-Jun fusion protein was utilized as the substrate for JNK3 kinase assay and GST SEK1 fusion protein was utilized as the substrate for MLK2 kinase assay. To generate GST-c-Jun or GST-SEK1 (K54R) fusion proteins, the cDNA fragment encoding the N-terminus of c-Jun 1–89 amino acid residues, or the full-length cDNA of SEK1, was subcloned into a pGEX vector. The vector was subsequently transformed into *E. Coli* and the *E. coli* carrying pGEX-Jun or PGX-SEK1 was grown in LB medium. Expression of these GST fusion proteins was induced by 0.1 mM isopropyl-b-D-thiogalactopyraside (IPTG). Cells were pelleted and resuspended in 1/60 culture volume of MT PBS (150 mM NaCl, 16 mM Na$_2$HPO$_4$, 4 mM NaH$_2$PO$_4$, pH 7.3) and then lysed by mild sonication after adding Triton X-100 to the final concentration of 1% followed by centrifugation at 10,000×g for 5 min at 4° C. The supernatant was mixed at room temperature in a 50 ml polypropylene tube on a rotating platform with 1–2 ml 50% glutathione agarose beads. After absorption for 2min, beads were collected by brief centrifugation at 500×g and washed three times with 50 ml MT PBS. The c-Jun or SEK1 GST fusion proteins were eluted by competition with free glutathione using 2×2 min washes twice with the same buffer, and stored. The purified GST fusion proteins were stored at −80° C. in MT PBS at 4° C. as a 50% solution.

Example 5

Transfection and INK in Vitro Kinase Assay

For an in vitro JNK kinase assay, including JNKI, JNK2 and JNK3, isolated JNK protein was used. Isolation may be accomplished by chromatographic purification from tissue or molecular transfection of host cells followed by isolation. For molecular isolation of JNK, a full length cDNA of either JNKI, JNK2 or JNK3 glutathione-S-transferase (GST) fusion construct was inserted into pGEX-2T vector and expressed in a host, such as a bacterial cell (e.g., DHI cell). The fusion protein was then purified from the host cell using standard techniques known to those skilled in the art. Isolation of the GST-fusion protein was accomplished using a glutathione affinity column. Approximately 5 μL of glutathione-Sepharose was used to recover the fusion protein. The resin was washed three times with lysis buffer (20 MM Tris-HCl, pH 8.0, 2 mM EDTA, 50 mM β-glycerophosphate, 1 mM Na$_2$PO$_4$, 1% Triton X-100, 10% glycerol, 1 mM phenylmethylsulfonyl fluoride (PMSF). 10 μg/mL leupeptin and 10 μg/mL aprotinin) and twice with detergent-free lysis buffer. The GST-fusion protein was eluted from the resin with 100 μL of 5 mM glutathione in a detergent-free lysis buffer.

The in vitro kinase reaction was carried out at 30° C. for 15 minutes in a kinase mixture containing 0.5 μg of GST-JNK3, 1 μg of GST-c-Jun, 2.5 mM ATP and 5 μCi of [γ-$^{32}$P] ATP with or without a test compound in 20 μL of kinase buffer (20 mM HEPES, pH 7.5, 15 mM MgCl$_2$, 15 mM β-glycerophosphate, 0.1 mM Na$_2$PO$_4$, 2 mM dithiothreitol). The reaction was terminated by adding 20 μL of SDS sample buffer (Laemmeli buffer). The phosphorylation was detected by SDS-PAGE, and the amount of $^{32}$P incorporated was quantified with an image analyzer. Effectiveness of the test compound as an inhibitor of JNK correlated with inhibitor of $^{32}$P incorporated GST-c-Jun.

Example 6

Transfection and MLK2 or MLK3 in Vitro Kinase Assay

For an in vitro MLK 2 or 3 kinase assay, isolated MLK2 protein is used. Isolation may be accomplished by chromatographic purification from tissue or molecular transfection of host cells followed by isolation. For molecular isolation of MLK, a full length cDNA of either MLK2 or MLK3 glutathione-S-transferase (hereinafter GST) fusion construct was inserted into pEGB vector and expressed in 293 host cells using lipofectin, as described above for transfection of mutated huntingtin into HN33 cells. Forty eight hours after transfection, the cells were lysed using 0.5 ml at a lysis buffer (20mM Tris-HCl, PH 8.0, 2 mM EDTA, 50 mM βglycerophosphate, 1 mM Na$_2$ VO$_4$, 1% Triton X-100, 10% glycerol, 1 mM phenylmethylsulfonyl fluoride (PMSF), 10 μg/ml leupeptin and 10 μg/ml aprotinin). The fusion protein was then purified from the host cell using standard techniques known to those skilled in the art. Isolation of the GST-fusion protein was accomplished using a glutathione affinity column. Approximately 5μL of glutathione-Sepharose was used to recover the fusion protein. The resin was washed three times with lysis buffer and twice with detergent-free lysis buffer. The GST-fusion protein was eluted from the resin with 100 μL of 5 mM glutathione in a detergent-free lysis buffer.

The in vitro kinase reaction was carried out at 30° C. for 45 minutes in a 20 μL kinase mixture containing 1 μg of GST-MLK2 or MLK3, 1 μg of GST-SEK1 (K54R), 2 mM ATP and 5 μCi or [γ−$^{32}$P] ATP in the absence or presence of a test compound in the kinase buffer (20 mM HEPES, pH 7.5, 15 mM MgCl$_2$, 15 mM β-glycerophoshate, 0.1 mM Na$_2$VO$_4$, 2 mM dithiothreitol). The reaction was terminated by adding 20 μL of SDS sample buffer (Laemmeli buffer). The phosphorylation was detected by SDS-PAGE, and the amount of $^{32}$P incorporated was quantified with an image analyzer. Effectiveness of the test compound as an inhibitor of MLK2 or MLK3 correlated with inhibition of $^{32}$P incorporated GST-SEK1 (K54R).

Example 7

MLK2 Immunocomplex Kinase Assay

An MLK2immunocomplex kinase assay was used to screen for the MLK 2or 3 inhibitor and to dertermine the specificity of the identified MLK inhibitor. The full-length cDNA of MLK 2 or 3 was inserted into pRK5 vector and tagged with c-myc at the C-terminus. 293 embryonic cells were grown in DMEM with 10% FBS in a 6-well dish and then were transfected with pRK5MLK2 using lipofectin as described above. Forty-eight hours after transfection, cells were lysed with 0.5 ml of a lysis buffer (20mM Tris-HCI, pH 8.0, 2 mM EDTA, 50 mM β-glycerophosphate, 1 mM Na$_2$VO$_4$, 1% Triton X-100, 10% glycerol, 1 mM phenylmethylsulfonyl fluoride (PMSF), 10 μg/ml leupeptin, and 10 μg/ml aprotinin) and the lysates were incubated with anti-c-myc tag antibody 9E10 for 1 hour and 20 μl of a mixture (50×50) or protein G and A-Sepharose resin was add and continued to incubate for another 2–4 hours. The resin was washed twice with lysis buffer and twice with detergent-free lysis buffer. The pellet was then resuspended in 20 μl of kinase buffer (20 mM HEPES, pH 7.5, 15 mM MgCl$_2$, 15 mM β-glycerophosphate, 0.1 mM Na$_2$VO$_4$, 2 mM dithiothreitol, 25 μM ATP, 5 μCi of [γ$^{32}$P] ATP, and 0.5 μg of SEK1(K54R) GST fusion proteins in the presence or absence (control) of 1 nM to 10 μM of a mixture of compounds or the identified compounds. The kinase reaction was carried out at 30° C. for 20 min. and stopped by adding 20 μl of SDS sample buffer. The phosphorylation is detected by SDS-PAGE, and the amount of $^{32}$P incorporated is quantified with an image analyzer. If a compound is effective to inhibit MLKs, the amount of $^{32}$P incorporated is significantly reduced or totally inhibited.

Example 8

96-Well Cell Based Assay

HN33 cells (~60% of confluence), plated on a 96-well plate, were grown in DMEM-F12 medium supplemented with 10% of fetal bovine serum (FBS). Prior to transfection, the medium was removed and cells were washed with serum-free medium once and 50 μl of DMEM-F12 medium with 1% of FBS was added. The full-length huntingtin expression plasmid containing 16 (control),48 or 89 CAG repeats or lipofectin solution were diluted with HBS first and mixed 1×1 volume and the mixture was incubated at room temperature for 15 min. Ten μl of the DNA-lipofectin mixture was added to the culture medium. A mixture of compound from a chemical library was added 6 hours after transfection. Twelve hours after transfection, additional FBS was added to the final concentration of 10%. Forty-eight hours after transfection, cells were washed with PBS once and fixed with 4% paraformaldehyde dissolved in PBS and permeabilized with 1% Triton X100 in PBS containing 1% sodium citrate. Cell were then rinsed twice with PBS containing 1% BSA and cells were incubated with 25 μl of TUNEL reaction solution for 1 hour at a 37° C. cell culture incubator. Cell were rinsed with PRS for three times and 25 μl of converter-AP solution was added and cells are returned to the incubator and incubated for 30 min. Cells were rinsed three times with PBS with 1% BSA and cells were incubated in a BCIP solution for 1–5 min at room temperature and rinsed three times with PBS and analyzed under light microscope.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for assessing a compound's ability to prevent neuronal cell death, comprising:
   a) contacting a compound with cultured neuronal cells having activated MLK activity, wherein activated MLK activity is selected from the group consisting of MLK1 activity, MLK2 activity, MLK3 activity, and wherein the activity is a kinase activity; and
   b) determining the number of cultured neuronal cells that die; wherein a decreased number of dead cultured cells in the presence of the compound compared to the number of dead cultured neuronal cells in the absence of the compound is indicative of the compound's ability to prevent neuronal cell death.

2. The method of claim 1, wherein the neuronal cells are expressing a mutated protein selected from the group consisting of polyglutamine stretch-expanded huntingtin and C-terminal 100 amino acids of amyloid precursor protein, or the neuronal cells are treated with a neurotoxin to induce apoptosis.

3. The method of claim 2, wherein the neuronal cells are HN33 cells.

4. The method of claim 2, wherein the neurotoxin is glutarnate, quinolinic acid or kainic acid.

5. The method of claim 1, wherein the neuronal cells are apoptotic neurons.

6. A method for assessing a compound's ability to prevent neuronal cell death, comprising:
   a) contacting a compound with cultured neuronal cells expressing a mutated protein selected from the group consisting of polyglutamine stretch-expanded huntingtin and C-terminal 100 amino acids of amyloid precursor protein, or with neuronal cells treated with a neurotoxin to induce neuronal cell death; and
   b) determining the number of cultured neuronal cells that die; wherein a decreased number of dead cultured neuronal cells in the presence of the compound compared to the number of dead cultured cells in the absence of the compound is indicative of the compound's ability to prevent neuronal cell death.

7. The method of claim 6, wherein the neuronal cells are HN33 cells.

8. A method for assessing the ability of a compound to prevent neuronal cell death, comprising:
   a) contacting a compound with cultured neuronal cells having activated MLK activity, wherein the activated MLK activity is selected from the group consisting of MLK1 activity, MLK2 activity, MLK3 activity, and wherein the activity is a kinase activity;
   b) contacting, in the presence of the compound, surviving cells from step (a) with an agent that induces apoptosis; and
   c) comparing the level of apoptosis in the cells in the presence of the compound with the level of apoptosis in the cells in the absence of the compound; wherein the compound is a potentially useful drug for treating mammals when the level of apoptosis in the cells in the presence of the compound is less than the level of apoptosis in the cells in the absence of the compound.

9. The method of claim 8, wherein the apoptotic agent is a neurotoxin.

10. The method of claim 9, wherein the neurotoxin is glutamate, quinolinic acid or kainic acid.

11. The method of claim 8, wherein step (b) is performed by transfecting the surviving neuronal cells with nucleic acid encoding a mutated form of huntingtin or amyloid precursor protein.

12. The method of claim 8, wherein the neuronal cells are HN33 cells.

13. A method for assessing the ability of a compound to inhibit MLK activity and to prevent neuronal cell death, comprising the steps of:
   a) contacting a compound with a MLK protein and a substrate therefor, wherein the MLK protein is selected from the group consisting of MLK1, MLK2, MLK3 and combinations thereof;
   b) measuring the level of MLK activity, wherein the MLK activity is a kinase activity;
   c) comparing the level of MLK activity in the presence of the compound with the level of MLK activity in the absence of the compound, wherein a decrease in MLK activity in the presence of the compound is indicative that the compound has an ability to inhibit MLK activity;
   d) contacting the compound having an ability to inhibit MLK activity with cultured neuronal cells having activated MLK activity, wherein the activated MLK activity is kinase activity; and
   e) comparing the occurrence of apoptosis in the cultured neuronal cells in the presence of the compound with the occurrence of apoptosis in the cultured neuronal cells in the absence of the compound; wherein the compound having an ability to inhibit MLK activity has the ability to prevent neuronal cell death when the occurrence of apoptosis in the cultured neuronal cells in the presence of the compound is less than the occurrence of apoptosis in the cultured neuronal cells in the absence of the compound.

* * * * *

UNITED STATES PATENT AND TRADEMARK OFFICE
CERTIFICATE OF CORRECTION

PATENT NO.    : 6,811,992 B1
DATED         : November 16, 2004
INVENTOR(S)   : Ya Fang Liu It is certified that error appears in the above-identified patent and that said Letters Patent is hereby corrected as shown below:

Title page,
Item [54], Title, should read:
-- METHOD FOR IDENTIFYING JNK AND MLK INHIBITORS FOR TREATMENT OF NEUROLOGICAL CONDITIONS --.

Column 23,
Line 57, delete "glutarnate" and replace with -- glutamate --.

Signed and Sealed this

Twenty-fourth Day of January, 2006

JON W. DUDAS
*Director of the United States Patent and Trademark Office*

UNITED STATES PATENT AND TRADEMARK OFFICE
CERTIFICATE OF CORRECTION

PATENT NO. : 6,811,992 B1 Page 1 of 1
APPLICATION NO. : 09/156367
DATED : November 2, 2004
INVENTOR(S) : Ya Fang Liu It is certified that error appears in the above-identified patent and that said Letters Patent is hereby corrected as shown below:

<u>Title page,</u>
Item [54], Title, should read:
-- METHOD FOR IDENTIFYING JNK AND MLK INHIBITORS FOR TREATMENT OF NEUROLOGICAL CONDITIONS --.

<u>Column 23,</u>
Line 57, delete "glutarmate" and replace wth -- glutamate --.

This certificate supersedes Certificate of Correction issued January 24, 2006.

Signed and Sealed this

Twenty-seventh Day of June, 2006

JON W. DUDAS
*Director of the United States Patent and Trademark Office*